(12) United States Patent
Aga et al.

(10) Patent No.: US 6,524,625 B2
(45) Date of Patent: *Feb. 25, 2003

(54) PHYSIOLOGICALLY ACTIVE EXTRACT OBTAINED FROM INDIGO PLANT POLYGONUM TINCTORIUM

(75) Inventors: Hajime Aga, Okayama (JP); Shigeyuki Arai, Okayama (JP); Shigeharu Fukuda, Okayama (JP); Toshio Kunikata, Okayama (JP); Masashi Kurimoto, Okayama (JP)

(73) Assignee: Kabushiki Kaisha Hayashibara Seibutsu Kagaku Kenkyuto, Okayama (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/339,928

(22) Filed: Jun. 25, 1999

(65) Prior Publication Data

US 2002/0068094 A1 Jun. 6, 2002

(30) Foreign Application Priority Data

Jun. 30, 1998 (JP) ............................................. 10-183608
Oct. 28, 1998 (JP) ............................................. 10-306776
Apr. 19, 1999 (JP) ............................................. 11-110852
May 14, 1999 (JP) ............................................. 11-133597

(51) Int. Cl.$^7$ ...................... A65K 35/78; A61K 31/495; A61K 31/50; A61K 31/505
(52) U.S. Cl. ........................ 424/725; 514/250; 514/253; 514/254; 514/257
(58) Field of Search ................ 424/195.1, 725; 514/250, 253, 254, 257

(56) References Cited

U.S. PATENT DOCUMENTS 5,441,955 A * 8/1995 Baker et al. ................. 514/250
5,837,257 A * 11/1998 Tsai et al. ................. 424/195.1

FOREIGN PATENT DOCUMENTS

| GB | 2330305 | | 4/1999 |
| JP | 55047684 | * | 4/1980 |
| JP | 4124137 | * | 4/1992 |

OTHER PUBLICATIONS

Honda et al. Planta Med. vol. 38, No. 3, pp. 275–276, Mar. 1980.*
Mitscher et al. Medicinal Res. Rev. vol. 18, No. 6, pp. 363–374, abstract enclosed, Nov. 1998.*
Registry Database profile on the chemical compound tryptanthrin, 2000.*
Patent Abstracts of Japan, vol. 016, No. 383, (1992).
Nicoletti, J., et al., "A Rapid and Simple Method for $_{Mea}$suring Thymocyte Apoptosis by Propidium Iodide Staining and Flow Cytometry," *Journal of Immunological Methods* 139:271–279 (1991).
Riken Gene Bank, "General Catalog–Animal Cells, Plant Cells, DNA Clones, Libraries, and Bioinformatice" 3:(May 1997).
"ATTC Bacteria and Bacteriophages" 19th Edition (1996), American Type Culture Collection.
"ATTC Cell Lines and Hybridomas" 8th Edition (1994), American Type Culture Collection.
Institute for Fermentation, Osaka (IFO), "List of Cultures" *Microorganisms* 9:(1992).

* cited by examiner

*Primary Examiner*—Christopher R. Tate
(74) *Attorney, Agent, or Firm*—Browdy and Neimark, PLLC

(57) ABSTRACT

A physiologically active extract comprising an ethyl acetate-soluble ingredient of an indigo plant, which is obtainable by soaking a raw indigo plant in an organic solvent used for extraction. The ethyl acetate-soluble ingredient includes tryptanthrin, 3,5,4'-trihydroxy-6,7-methylenedioxy-flavone, kaempferol, 3,5,7,4'-tetrahydroxy-6-methoxy-flavone, gallic acid, caffeic acid, indirubin, pheophorbide a, and methylpheophorbide a.

20 Claims, 3 Drawing Sheets

PHYSIOLOGICALLY ACTIVE EXTRACT OBTAINED FROM INDIGO PLANT POLYGONUM TINCTORIUM

BACKGROUND OF THE INVENTION

1. Field of the Invention

The present invention relates to a novel physiologically active extract from a plant, and more particularly to a physiologically active extract comprising an ethyl acetate-soluble ingredient from a raw indigo plant, its process, and uses.

2. Description of the Prior Art

Indigo plant or *Polygonum tinctorium Lour.* is an annual plant of the family polygonum classified into a dicotyledonous plant, and the place of origin is South Vietnam. It is said that the plant was brought to Japan from China before the 7th century as a plant for dying deep blue, together with the dying technique, and is now being cultivated in and around Tokushima—prefecture in Japan. In the old days, people believed that the leaves and seeds of the indigo plant contained useful physiologically active ingredients and were used as a crude drug after being dried under the sun into dried indigo leaves and seeds. As described in pages 5 to 7 of *"Nippon-Yakuso-Zensho"* (Encyclopedia of Japanese Medicinal Plants), edited by Mizuo Mizuno, published on Feb. 22, 1995 by Shin-Nihon-Hoki-Shuppan Publisher, Tokyo, Japan, the indigo plant was merely known for its anti-inflammatory-, alleviation-, and detoxification-actions; such physiological actions can only be expected when used in the form of an infusion prepared by soaking the indigo leaves and seeds in hot water.

At present being substantially free from inconvenience of clothes, foods and homes, people, including those of younger ages, are beginning to pay a striking attention to their health, more particularly to crude drugs which can be easily used daily without doctors' prescriptions. This can be seen from the fact that articles on crude drugs are published, and various types of health foods and supplemental health foods are flooding groceries and pharmacies. Generally, crude drugs have a mild action and a lesser side effect as advantageous features but have a different sensitivity for individuals as a demerit; the establishment of a novel crude drug with diversified physiological activities will be greatly required for answering the users' demands.

SUMMARY OF THE INVENTION

In view of the foregoing, the present invention aims to provide a novel physiologically active extract from a plant, which exerts diversified physiological actions.

The present invention further aims to provide a process for producing the physiologically active extract.

The present invention also aims to provide a physiologically active composition containing the physiologically active extract.

The present inventors' energetic study revealed that a novel physiologically active extract from indigo plant or an extract, obtainable by soaking a raw indigo plant in an organic solvent to extract ethyl acetate-soluble ingredients, exerts in mammals and humans diversified physiological actions including antiseptic-, antiviral-, antitumor-, radical entrapping-, apoptosis controlling-, and cytokine production controlling-, and cytokine production inhibitory-actions, as well as expression inhibitory action on nitrogen monoxide synthetic enzymes. They also found that the extract does not substantially show side effects in mammals and humans and it can be used safely in foods, cosmetics, and pharmaceuticals for humans.

The present invention solves the first object of the present invention by providing a physiologically active extract comprising an ethyl acetate-soluble ingredient from a raw indigo plant.

The present invention solves the second object of the present invention by providing a process for producing a physiologically active extract comprising the ethyl acetate-soluble ingredient from a raw indigo plant, characterized in that it comprises the steps of soaking the indigo plant in an organic solvent to extract the ethyl acetate-soluble ingredient from the plant, and collecting the extract.

The present invention solves the third object of the present invention by providing a physiologically active composition comprising the ethyl acetate-soluble ingredient.

As described already, it is well known that the water-extracted leaves and seeds of indigo plant, which are indigo plant products dried under the sun, exert anti-inflammatory-, alleviation-, and detoxification-actions; It is an unexpected finding that ethyl acetate-soluble ingredients, obtained by treating directly a raw indigo plant with an organic solvent, do exert the aforesaid diversified physiological actions. The present invention was made based on the finding.

BRIEF DESCRIPTION OF THE ACCOMPANYING DRAWINGS

DETAILED DESCRIPTION OF THE INVENTION

Figure 1:
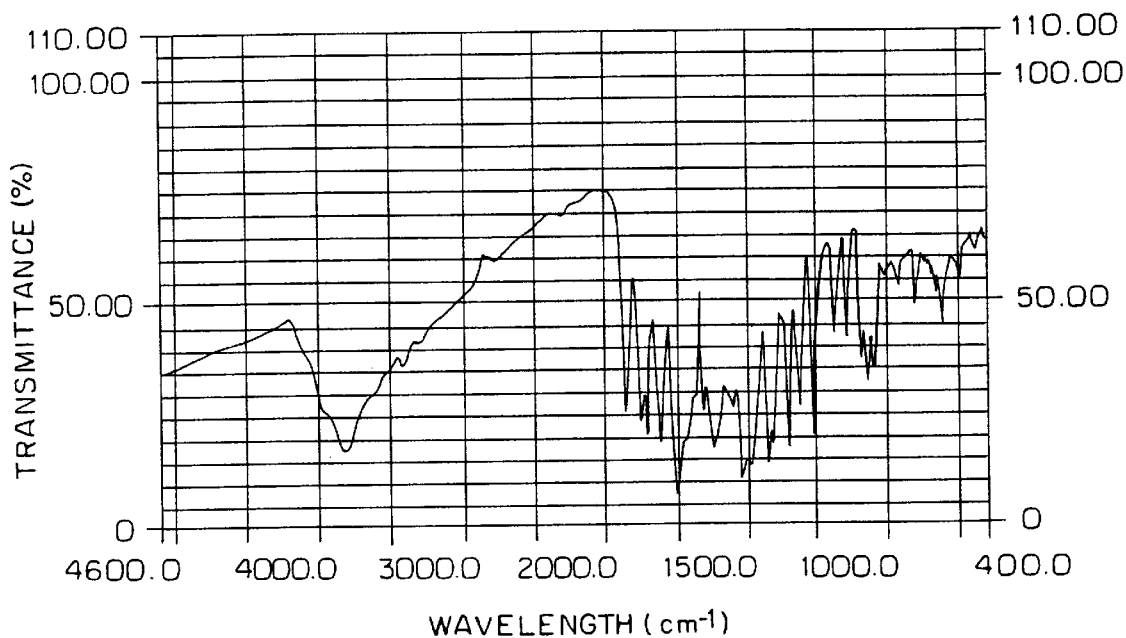
FIG. 1 is an infrared absorption spectrum of 3,5,4'-trihydroxy-6,7-methylenedioxy-flavone, i.e., Compound 2.

Now explaining the preferred embodiments according to the present invention, the invention relates to an indigo plant, an annual plant of the family polygonum classified into a dicotyledonous plant with a botanical name of *Polygonum tinctorium*. The wording "a raw indigo plant" as referred to in the present invention means a living raw indigo plant which is not substantially dried and perished. As long as being in such conditions, any one of indigo plants can be used in the present invention independently of their types and forms such as the whole plant bodies and specific parts of their leaves, stems and seeds. Most preferably used are fresh aerial parts of indigo plant, especially, those obtained from the plant before ripping.

The present physiologically active extract is prepared by soaking a raw indigo plant in an organic solvent to extract an ethyl acetate-soluble ingredient from the plant, and collecting the extract; A part or the whole of a raw indigo plant is washed with water to remove impurities, and if necessary further cut, pulverized and/or pressed, and then soaked in an appropriate organic solvent usually in an amount of 1 to 100 fold volumes of the raw indigo plant for 0.1–100 hours under optional heating conditions. The organic solvents used in the present invention include hydrophilic and hydrophobic organic solvents such as methanol, ethanol, n-propanol, isopropanol, n-butanol, isobutanol, t-butanol, methyl ether, ethyl ether, tetrahydro-furan, chloroform n-hexane, acetone, and ethyl acetate. The organic solvents can be used in combination depending on use. In the case of using the present physiologically active extract without substantially purifying, mixtures of water and ethanol or methanol can be preferably used even though the extraction efficiency of the ethyl acetate-soluble ingredients rather decreases.

The physiologically active extract thus obtained can be used intact, and usually it is further treated to remove impurities with filtration, separation, separatory sedimentation, decantation and/or centrifugation, and then treated to remove organic solvents depending on the types of the organic solvents used and the final use of the extract. Depending on the types of the organic solvents, the present physiologically active extract contains as ethyl acetate-soluble ingredients 6,12-dihydro -6,12-dioxoindolo[2,1-b] quinazoline; 3,5,4'-trihydroxy -6,7-methylenedioxy-flavone; kaempferol; 3,5,7,4'-tetrahydroxy-6-methoxy-flavone; gallic acid; caffeic acid; 3-(1,3-dihydro-3-oxo -2H-indol-2-ylidene)-1,3-dihydro-2H-indol-2-one; [3S-(3$\alpha$, 4$\beta$, 21$\beta$)]9-ethyl-14-ethyl-21-(methoxycarbonyl)-4,8,13,18-tetramethyl -20-oxo-3-phorbinepropanoic acid); and/or [3S-(3$\alpha$, 4$\beta$, 21$\beta$)]9-ethyl-14-ethyl-21-(methoxycarbonyl)-4,8,13,18- tetramethyl -20-oxo-3-phorbinepropanoic acid methyl ester in an amount of at least 0.01%, on a dry solid basis (d.s.b.). These ingredients exert an effective antiseptic-, antiviral-, antitumor-, radical entrapping-, apoptosis controlling-, and/or cytokine production controlling- or inhibitory-actions in mammals and humans. For example, when used in pharmaceuticals that require the present physiologically active extract in a relatively-highly purified form, the ethyl acetate-soluble ingredients should previously be separated from the extract by the methods generally used for purifying indole derivatives and flavone compounds. Examples of the purification methods are salting out, dialysis, filtration, concentration, liquid separation, separatory sedimentation, decantation, liquid chromatography, gas chromatography, high-performance liquid chromatography, and crystallization. These methods can be used in an appropriate combination, if necessary. The ethyl acetate-soluble ingredients each have different levels of physiological actions and action spectra; they should preferably be incorporated intact into desired products in the same proportion as they are present in the extracts when used in the fields including foods that permit the use of the ingredients without being separated into each ingredient. The physiologically active ingredients have a merit that they exert diversified physiological actions when used in such forms. In the cause of incorporating the ingredients into pharmaceuticals such as injections, depending on diseases susceptive to the ingredients, one or more of the ingredients can be arbitrarily used after separation or without separation. The methods as described in the above are just the preferred examples for preparing the present physiologically active extract, and they do not limit the present physiologically active extract as long as the extract contains the ethyl acetate-soluble ingredients.

The present physiologically active extract containing ethyl acetate-soluble ingredients have at least one or more of the following properties and exert diversified physiological actions on mammals and humans:

(1) Inhibiting the growth of gram-positive and gram-negative microorganisms including *Helicobacter pylori* known as microorganisms which induce gastritis, gastric ulcer, duodenal ulcer, and gastric cancer;

(2) Inhibiting the growth of pathogenic virus including influenza virus, vesicular stomatitis virus, herpes simplex virus, vaccinia virus, and cytomegalovirus;

(3) Inhibiting the growth of tumor cells of incurable tumors including leukemia-, gastric cancer-, and lung cancer-cells;

(4) Entrapping radicals derived from active oxygen and lipoperoxide that induce malignant tumors, myocardial infarction, cerebral apoplexy, rheumatism, lifestyle related diseases including geriatric diseases, renal disorders, stresses, and aging;

(5) Acting on normal and abnormal B-cells, T-cells, nerve cells, epithelial cells of digestive tracts, stem cells of digestive tracts, vascular endothelial cells, skin cells, etc., to regulate the apoptosis of the above cells within normal conditions and to treat/prevent the diseases of digestive organs, circulatory organs, eye, ear, norse, throat, skin, nerve, and bone;

(6) Controlling the production of cytokines including interferon-$\gamma$ and interleukin 10, by immuno-competent cells, which relate to the determination of the balance in vivo between type 1 helper T-cells (Th1) and type 2 helper T-cells (Th2) to control the balance within the normal conditions and to treat/prevent the diseases such as autoimmune diseases, and hepatic disorder-, renal disorder-, pancreatic disorder-, and graft-versus-host reaction-related diseases; and (7) Inhibiting the expression of nitrogen monoxide synthetic enzymes by cells in vivo, induced by cytokines and endotoxins, and inhibiting the formation of nitrogen monoxide to treat/prevent diseases such as autoimmune diseases, allergic diseases, inflammatory diseases, malignant tumors, renal disorders, and lung disorders.

The present physiologically active extract may contain angiogenic inhibitory substances which deeply relate to the tumor proliferation in vivo. The above physiological actions (1) to (6) can be confirmed by the methods of later described Experiments. For example, the expression inhibitory action on nitrogen monoxide synthetic enzymes can be confirmed by testing with conventional method using antibodies against the enzymes the influence of the addition of the present physiologically active extract on the expression of the enzymes, which are called generally "induction-type nitrogen monoxide synthetic enzymes" or "INOS", in mouse peritoneal macrophages or cell lines from the macrophages, induced when cultured in the presence of interferon-$\gamma$ or lipopolysaccharides. Conventional studies such as the Griess method on the level of nitrogen monoxide in the above culture system will be revealing the formation inhibitory effect on nitrogen monoxide by the expression inhibition of the enzymes. The present physiologically active extract may further exert an action of inhibiting angiogenesis relating deeply to the proliferation of tumors in vivo. The present extract may also act on the in vivo tissues' disorders that accompany the inflammation induced by gram positive-, gram negative-, and fungus-microorganisms and viruses; the invasion of or contact with proteins, organic compounds, and metals for living bodies; and by the occurrence of tumors to control the in vivo functions in such a manner that the present physiologically active extract inhibits the inflammation by inhibiting the production of inflammatory cytokines including interferon-$\gamma$ and interleukin-1. Because of these diversified physiological actions, the present physiologically active extract also has a property of improving the sleep disturbance caused by the incidence of diseases. Thus the present physiologically active extract can be arbitrarily used in food-, cosmetic-, and pharmaceutical-industries as a crude drug that exerts a mild antiseptic-, antiviral-, antitumor-, radical entrapping-, apoptosis controlling-, cytokine production controlling-, cytokine production inhibiting-, angiogenic inhibitory-, sleep disturbance improving-, in vivo function controlling-actions, and/or an action for inhibiting the expression of nitrogen monoxide synthetic-enzyme.

With these properties, the present physiologically active extract can be arbitrarily used in the fields of foods, cosmetics, and pharmaceuticals as a crude drug that exerts a moderate antiseptic-, antiviral-, antitumor-, radical entrapping-, and/or apoptosis controlling-actions in both healthy- and sick or wounded-individuals.

Now explaining the uses in each of the above fields, the present physiologically active extract can be used in the field of foods in combination with one or more materials and/or ingredients used in general in food products to ease the intake of the extract; Water, alcohols, amylaceous substances, proteins, fibers, saccharides, lipids, fatty acids, vitamins, minerals, flavors, colors, sweeteners, seasonings, spices, and antiseptics. The resulting mixtures can be formulated into desired shapes and forms such as liquids, suspensions, creams, pastes, jellies, powders, granules, and other desired shapes, depending on the actual use of foods. For use in such foods, the present physiologically active extract is generally used in an amount of at least 0.01 w/w %, and preferably 0.1 w/w %.

The food products for which the present invention is arbitrarily applied are, for example, seasonings such as a soy sauce, powdered soy sauce, "miso", "funmatsu-miso" (a powdered miso), "moromi" (a refined sake), "hishio" (a refined soy sauce), "furikake" ( a seasoned fish meal), mayonnaise, dressing, vinegar, "sanbai-zu" (a sauce of sugar, soy sauce and vinegar), "funmatsusushi-su" (powdered vinegar for sushi), "tentsuyu" (a sauce for Japanese deep-fat fried food), "mentsuyu" (a sauce for Japanese vermicelli), sauce, catsup, "yakiniku-no-tare" (a sauce for Japanese grilled meat), curry roux, "chuka-no-moto" (an instant mix for Chinese dish), instant stew mix, instant soup mix, "dashi-no-moto" (an instant stock mix), mixed seasoning, "mirin" (a sweet sake), "shin-mirin" (a synthetic mirin), table sugar, and coffee sugar; "wagashi" (Japanese cakes) such as a "senbei" (a rice cracker), "arare" (a rice cake), "okoshi" (a millet-and-rice cake), fried dough cake, "gyuhi" (starch paste), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella, and "amedama" (a Japanese toffee); confectioneries such as a biscuit, cracker, cookie, pie, pudding, cream puff, waffle, sponge cake, doughnut, chocolate, chewing gum, caramel, candy, and gummy jelly; frozen desserts such as an ice cream, ice candy, and sherbet; syrups such as a "korimitsu" (a sugar syrup for shaved ice); spreads and pastes such as a butter cream, custard cream, flour paste, peanut paste, and fruit paste; processed fruits and vegetables such as a jam, marmalade, "syrup-zuke" (a fruit pickle), and "toka" (a conserve); processed cereal foods such as a bun, noodle, cooked rice, and artificial meat; oil and fat foods such as a salad oil and margarine; pickles and pickled products such as a "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); premixes for pickles and pickled products such as a "takuan-zuke-no-moto" (a premix for pickled radish), and "hakusai-zuke-no-moto" (a premix for fresh white rape pickles); meat products such as a ham and sausage; products of fish meat such as a fish ham, fish sausage, "kamaboko" (a steamed fish paste), "chikuwa" (a kind of fish paste), and floated-type kamaboko (a Japanese deep-fat fried fish paste); "chinmi" (relishes) such as an "uni-no-shiokara" (salted guts of sea urchin), "ika-no-shiokara" (salted guts of squid), "su-konbu" (a processed tangle), "saki-surume" (dried squid strips), and "fugu-no-mirin-boshi" (a dried mirin-seasoned swellfish); boiled foods such as those cooked with agricultural products, livestocks, and fisheries; daily dishes such as a boiled food, grilled food, fry, fried food, steamed food, and dishes dressed with sauce; frozen foods such as a shrimp for frying, croquette, shao-mai, "gyoza" (fried or steamed dumpling stuffed with minced pork)), "harumaki" (a kind of Chinese dish), hamburger stake, meat ball, fish hamburger, and fish ball; retort foods such as a hamburger, meat ball, rice boiled together with red beans, rice boiled with beef or chicken, gruel of unpolished rice, curry, meat sauce, demiglace sauce, potage soup, consomme soup, stew, Japanese hotchpotch, "happosai" (a kind of Chinese vegetable), boiled bean, grilled chicken, pot-steamed hotchpotch, boiled chestnut, and vegetable boiled in water; egg and milk products such as a "kinshi-tamago" (a stripped egg roll), milk beverage, butter, and cheese; canned and bottled products such as those of meats, fish meats, fruits, and vegetables; alcohols such as synthetic sake, sake, wine, and liquor; soft drinks such as coffee, cocoa, juice, green tea, tea, Oolong tea, mineral beverage, carbonated beverage, sour milk beverage, and beverage containing lactic acid bacteria; and instant food products such as instant pudding mix, instant hot cake mix, instant juice, "sokuseki-shiruco" (an instant mix of adzuki-bean soup with rice cake), and instant soup mix. The present physiologically active extract has a property of entrapping radicals formed in vivo so that it can be advantageously used in health foods and supplemental health-foods directed for preventing lifestyle related diseases or geriatric diseases, carcinogenesis, and aging. In addition to foods for humans, the present extract can be also used in feeds and pet foods for animals such as domestic animals, poultry, honey bees, silk worms, and fish.

In the field of cosmetics, the present physiologically active extract can be used in combination with the following ingredients that ease the administration of the extract, for example, oily bases, water-soluble bases, flavors, colors, dyes, refrigerants, humectants, emollients, emulsifiers, gelation agents, viscosity enhancers, softening agents, solubilizing agents, surfactants, stabilizers for foaming, clearances, antioxidants, adipositas agents, putrefactive agents, coating-forming agents, and spraying agents. The present extract can be also used by mixing with one or more medicaments such as vitamins, amino acids, peptides, hormones, extracts, vasodilators, bloodcirculation-promotingagents, cell-activating agents, germicides, anti-inflammatory drugs, urtication-preventing agents, astringents, skin-function-promoting agents, and keratolytics. The resulting mixtures can be processed into products in the form of a liquid, emulsion, cream, paste, powder, granule, or a solid with another desired shape. Depending on use, the present physiologically active compositions as cosmetics usually contain at least 0.005 w/w %, and preferably at least 0.05 w/w % of the present physiologically active extract.

Examples of the cosmetics for which the present physiologically active extract can be arbitrarily applied are those for hairs such as hair restorers and hair growth-promoting agents, pomades, hair sticks, hair oils, hair creams, hair solids, hair liquids, hair set lotions, hair styling-jells, hair water-greases, hair blows, hair aerosols, hair liquids for permanent wave, and hair dyes; those for washing such as shampoos for hair and body, hair rinses, hair-washing soaps, cosmetic soaps, and creasing foams; those for skins such as cosmetic water, creams, milky lotions, lotions, packs, foundations, lip sticks, rouges, eye liners, mascara, eye shadows, eyebrow pencils, manicures, and powders; those for oral uses such as tooth powders, moisturized dentifrices, toothpastes, tooth washes, medical dentifrices, cachous, and gargles; and another cosmetics such as sunscreens, shaving cosmetics, bath cosmetics, perfumes, eau de Colongnes, underarm deodorants, baby powders, eye lotions, and bleaching creams. In the case of cosmetics for skin and hair, incorporation into the present physiologically active extract an about 0.001 w/w % to about 10 w/w % of α-glucosyl bioflavonoids such as α-glucosyl rutin, α-glucosyl hesperidin, and α-glucosyl naringin can supplement nutrition to the skin and promote metabolism in living bodies, resulting in an easy exertion of the effects of the present physiologically active extract. Incorporation of, as humectants, saccharides or sugar alcohols with a moisture-imparting action such as maltose, trehalose, and maltitol in an adequate amount, preferably, not higher than one w/w %, adequately moistens the skin, scalp and/or hair and allows the present physiologically active extract to exert its effect easily.

In the field of pharmaceuticals, the present physiologically active extract can be arbitrarily used to treat and/or prevent all the diseases, which are susceptive to the present ethyl acetate-soluble ingredient, including bacterial diseases, mycotic diseases, viral diseases, malignant tumors, hyperlipemias, and ischemic heart diseases; for example, digestive diseases, circulatory organs' diseases, urinary/genital organs' diseases, immune diseases, cranial nerve diseases, eye diseases, skin diseases, and diseases of nose, ear and throat. Examples of such diseases susceptive to the present physiologically active extract are bacterial diseases such as bacterial corneal ulcer, bacterial conjunctivitis, bacterial food poisoning, septic shock, endotoxin shock, bacterial endocarditis, bacterial meningitis, bacterial pneumonia, bacterial aneurysm, and bacterial cerebral aneurysm; viral diseases such as fungal meningitis, fungal corneal ulcer, fungal skin diseases, candidiasis, and tinea; viral diseases such as viral gastroenterocolitis, viral hepatitis, viral bronchitis, viral colon inflammatory, viral myocarditis, viral meningitis, viral enterocolitis, viral encephalitis, viral pneumonia, and AIDS; massive malignant tumors such as renal cell carcinoma, mycosis fungoides, and chronic granuloma; blood malignant tumors such as colonic cancer, rectal cancer, carcinoma of the colon and rectum, gastric cancer, thyroid carcinoma, cancer of the tongue, bladder carcinoma, cilium carcinoma, hepatoma, prostatic cancer, carcinoma uteri, cancer of pharynx, lung cancer, breast cancer, malignant melanoma, Kaposi's sarcoma, brain tumor, neuroblastoma, ovarian tumor, testicular tumor, pancreatic tumor, renal cancer, hypernephroma, hemangioendothelioma, adult T-cell leukemia (ATL), chronic myelogenous leukemia (CML), and malignant lymphoma; autoimmune-, allergic- and viral-diseases such as active chronic hepatitis, atrophic gastritis, autoimmune hemolytic anemia, Basedow disease, Behcet's syndrome, Crohn's disease, CRST syndrome, cold agglutinin hemolytic anemia, idiopathic ulcerative colitis, Goodpasture's syndrome, hyperthyroidism, chronic thyroiditis, inflammation of pulmonary alveoli, glomerulo-nephritis, idiopathic thrombocytopenic purpura, juvenile diabetes mellitus, insulin dependent diabetes mellitus, leukopenia, multi sclerosis, myasthenia gravis, paroxysmal cold hemoglobinuria, pernicious anemia, polyarteritis nodosa, polymyositis, primary biliary cirrhosis, rheumatic fever, rheumatoid arthritis, Sjögren's syndrome, sympathetic ophthalmia, progressive systemic sclerosis, Wegener granulomatosis, asthma, atopic dermatitis, bronchial asthma, graft-versus-host disease, allergic rhinitis, pollinosis. and allergy for bee's toxic; hepatic diseases such as alcoholic hepatitis, toxic hepatitis, viral cirrhosis, alcoholic cirrhosis, toxic cirrhosis, biliary cirrhosis, fatty liver, hepatic tumor, and hepatic vascular disorder; gallbladder/biliary tract diseases such as cholangitis, cholecystitis, primary sclerosing cholangitis, gallbladder tumor, and cancer of the bile duct; pancreatic diseases such as acute pancreatitis, chronic pancreatitis, pancreatic insufficiency, pancreatic tumor, and pancreatic cysts; circulatory organs' diseases such as ischemia, ischemic heart disease, cerebral ischemia, basilar artery migraine, abnormal vascularnet at the brain base, cerebral apoplexy, aneurysm of the brain base, arteriosclerosis, vascular endothelial disorder, noninsulin-dependent diabetes mellitus, occlusion of the mesenteric vessel, and superior mesenteric artery syndrome; nerve diseases such as Parkinson's disease, spinal atrophy, amyotrophic lateral sclerosis, Alzheimer's disease, dementia, cerebrovascular dementia, AIDS dementia, and Meningitis; digestive diseases such as peptic ulcer, peptic esophagus ulcer, intestinal polyp, intestinal adhesion, intestinal rigidity, and gastric ulcer; sleep disturbances caused by the incidence of mental diseases, central nervous system depressants, habitual alcohols, and the disorder of respiratory system; and other diseases induced by side effects accompanied by the administration of hypnotics.

In the field of pharmaceuticals, the present physiologically active extract can be used in an effective amount with the following agents commonly used in such a field; Anesthetics, hypnotic sedatives, anti-anxieties, antiepileptics, antipyretic antiphlogistics, stimulants, wake amines, anti-parkinson drugs, agents for psychoneuroses, agents for central nervous system, skeletal muscle relaxants, agents for autonomic nervous system, antispastic agents, drugs for eye, drugs for nose and ear, anti-vertiginous drugs, cardiotonics, antiarrhythmic drugs, diuretics, pressure reduction drugs, vasoconstrictors, coronary vaso-dilators, peripheral vasodilating drugs, hyper-lipemia drugs, breath stimulants, antitussive and expectorant drugs, bronchodilators, drugs for allergy, antidiarrheal drugs, drugs for intestinal disorders, peptic ulcer drugs, stomachic digestants, antacids, cholagogouses, pituitary hormone drugs, salivary gland hormones, thyroid hormone drugs, antithyroid drugs, anabolic steroids, corticosteroids, androgen drugs, estrogen drugs, corpus luteum hormone drugs, mixed hormones, urinary/genital organ drugs, anus drugs, surgical sterilizations/antiseptics, wound protectives, externals for purulent diseases, analgesics, antipruritics, astringents, antiphlogistics, externals for parasite skin diseases, skin-softening drugs, caustics, dental/oral drugs, vitamins, inorganic preparations, supplemental liquids, hemostatics, anticoagulation drugs, drugs for liver diseases, antidotes, habitual intoxication drugs, drugs for treatment of gout, enzyme preparations, diabetic drugs, antioncotics, antihistaminics, drugs for stimulation treatment, antibiotics, chemotherapeutics, biological preparations, anthelmintics, anti-Protozoas, drugs for preparations, X-ray contrast media, and diagnostic drugs. In addition, one or more of extracts, elixirs, capsules, granules, pills, ointments for eye, suspensions, emulsions, plasters, suppositories, powders, ethanol prepara-tions, tablets, syrups, infusions, decoctions, injections, tinctures, ophthalmic solutions, trochees, ointments, cataplasms, aromatic water, liniments, lemonades, fluidextracts, lotions, nasal drops, nasal nebulas, inhalants for lower airway, sustained release drugs for eye, oral mucosal patches, and enemas. Depending on the use and administration route or frequency, the dose of the present physiologically active extract is usually selected from 0.01 to 100 mg per adult per day.

The physiologically active extract according to the present invention is incorporated into desired compositions in a prescribed amount before completion of their processings by using the methods such as mixing, kneading, dissolving, soaking, sprinkling, applying, spraying, and injecting. The compounds, 6,12-dihydro-6,12-dioxoindolo[2,1-b]quinazoline; 3,5,4'-trihydroxy -6,7-methylenedioxy-flavone; kaempferol; 3,5,7,4'-tetrahydroxy -6-methoxy-flavone, gallic acid, caffeic acid; 3-(1,3-dihydro-3-oxo-2H-indol-2-ylidene)-1,3-dihydro-2H-indol-2-one; [3S-(3α, 4β, 21β)]9-ethyl-14-ethyl-21-(methoxycarbonyl) -4,8,13,18-tetramethyl-20-oxo-3-phorbinepropanoic acid); and/or [3S-(3α, 4β, 21β)]9-ethyl-14-ethyl-21-(methoxycarbonyl)-4,8,13,18-tetramethyl -20-oxo-3-phorbinepropanoic acid methyl ester, which are contained in the present physiologically active extract, are known compounds, and their synthetic methods are also known. When the content of the ethyl acetate-soluble ingredients in the physiologically active extract is below a desired level, those which are prepared separatory can be supplemented to the ingredients.

As described above, the present physiologically active extract has the aforesaid satisfactorily actions; it is effectively used not only in the above-identified fields but in other fields of an antiseptic, antiviral agent, antitumor agent, radical-entrapping agent, apoptosis-controlling agent, agents for controlling the production of cytokines, and agents for inhibiting the expression of nitrogen monoxide synthetic enzymes. For example, in the case of using as an antiseptic, the physiologically active extract can be arbitrarily used in the above fields and also used effectively in pasteurizing antibacterial compositions for daily products in general. In these compositions, if necessary, the present physiologically active extract can be appropriately used in combination with another antiseptics such as a propolis, ε-polylysine, benzoic acid, paraoxybutyl benzoate, sodium benzoate, glycine, potassium sorbate, myconazole, ketoconazole, and ethanol; flavors, colors, surfactants, buffers, metals, and metal salts, after dissolving them in appropriate solvents or diluents. These pasteurizing antibacterial compositions can be used in products such as office instruments, clothes, furniture, toys, electric products, bedclothings, and stationary products either by applying, sprinkling or spraying or by mixing, kneading, dissolving, injecting or soaking before completion of the desired products. In every product, the present physiologically active extract effectively exerts the desired antiseptic action.

The following experiments describe the physiological action of the present physiologically active extract:

Experiment 1
Preparation of physiologically active extract

Thirty kilograms of an aerial part of a raw indigo plant, grown in Aki-city, Shimane-prefecture, Japan, were harvested in July, pulverized, and extracted repeatedly three times at ambient temperature with 30–60 l ethyl acetate for each extraction. The resulting extracts were pooled and filtered with a filter paper, and the filtrate was collected, subjected to evaporation for removing ethyl acetate, and dried into a 168 g extract containing ethyl acetate-soluble ingredients from the indigo plant.

Experiment 2
Isolation of ethyl acetate-soluble ingredient

An extract, obtained by the method in Experiment 1, was suspended in 50 v/v % aqueous methanol solution, and the resulting solution was divided into eight portions which were then respectively charged on a column packed with 1,700 ml of "FS-1830", a gel for adsorption chromatography commercialized by Japan Organo Co., Ltd., Tokyo, Japan, and eluted from the column by feeding successively as eluants 60 v/v %, 70 v/v %, 80 v/v %, and 90 v/v % aqueous methanol solutions, methanol, and ethyl acetate in the same volume as the gel. The former and latter fractions, called Fraction 2 and Fraction 1 respectively, eluted from the column with 80 v/v % aqueous methanol solution; the latter fraction, Fraction 3, eluted from the column with 60 v/v % aqueous methanol solution; the latter fraction, Fraction 4, eluted from the column with 90 v/v % aqueous methanol solution; and the former and latter fractions, named Fraction 5 and Fraction 6 respectively, eluted from the column with methanol, were respectively subjected to evaporation to remove the solvents and dried into solid products.

2.6 g from 5.2 g of the solid product, obtained from Fraction 1, was suspended in 30 ml methanol, filtered under suction, and separated into a soluble fraction and an insoluble fraction (876 g). The soluble fraction was fed to a column packed with 1,350 ml silica gel, eluted from the column with a linear gradient of a solvent system of chloroform and methanol increasing step-wisely from a methanol concentration of 5 v/v % to 100 v/v % while collecting the eluate 450 ml a fraction. The 4th fraction was subjected to evaporation to remove solvent into a solid product, followed by suspending it in two milliliters of methanol and filtering the suspension while washing under suction into a 19.4 mg crystal of Compound 1. The above insoluble fraction was dissolved in an appropriate amount of methanol and allowed to stand at ambient temperature to obtain a 278 mg of a yellow needle-like crystal of Compound 2.

10.7 g of the solid product obtained from Fraction 2 was suspended in 40 ml methanol, and the solution was fed to a column packed with 1,520 ml of "SEPHADEX LH-20", a gel for adsorption chromatography commercialized by Pharmacia LKB Biotechnology AB, Uppsala, Sweden, and eluted from the column with methanol while collecting 190 ml aliquots of the eluate. For each of the 15th and 18th fractions, the solvents were respectively removed by evaporation and dried into solid products. Four hundred milligrams of the solid product from the 18th fraction was completely dissolved in about 210 ml of a solvent system of methanol and waster (=5:2 by volume). The solution was filtered with a 0.22 μm membrane filter, and the filtrate was allowed to stand at ambient temperature for three days to find a crystal. The resulting mixture was filtered using a conventional filter paper to collect a 89.3 mg crystal of Compound 3. Five hundred milligrams of the solid product, obtained from the 15th fraction, was suspended in 10 ml methanol and filtered to collect insoluble substances which were then admixed with and completely dissolved in 250 ml methanol. The solution was filtered with a 0.22 μm membrane filter, allowed to stand at ambient temperature for seven days to find a crystal, and subjected to filtration using a commonly used filter paper to collect a 252.3 mg crystal of Compound 4.

11.8 g of the solid product obtained from Fraction 3 was suspended in 40 ml methanol, and the solution was fed to a column packed with 1,680 ml of "SEPHADEX LH-20", a gel for adsorption chromatography commercialized by Pharmacia LKB Biotechnology AB, Uppsala, Sweden, and eluted from the column with methanol while collecting the eluate 560 ml a fraction. The 4th fraction was subjected to evaporation to remove the solvent and dried into a solid product. The solid product was dissolved in 10 ml methanol, and the solution was fed to a column packed with 480 ml of "FS-1830", a gel for adsorption chromatography commercialized by Japan Organo Co., Ltd., Tokyo, Japan, eluted by successively feeding to the column 0, 10, 20, 30, 40, 50, 60 and 70 v/v % aqueous methanol solutions in a respective volume of 480 ml, and further eluted with 960 ml methanol. The eluate was fractionated 240 ml a fraction, and the 5th fraction was subjected to evaporation to remove the solvent and dried into a 150 mg solid product. The product thus obtained was dissolved in 300 ml ethyl acetate, and the solution was filtered with a 0.22 μm membrane filter. The filtrate was allowed to stand at ambient temperature for seven days to find a crystal, and the mixture was filtered with a commonly used filter paper to collect a 18.7 mg crystal of Compound 5. The 9th fraction eluted from the column of "FS-1830" was evaporated to remove the solvent and dried into a 500 mg solid product. Then the solid product was dissolved in 0.5 ml ethyl acetate, fed to a column packed with 40 ml of "SILICAGEL 60K650", a gel for adsorption chromatography commercialized by Katayama Chemical Industries Co., Ltd., Tokyo, Japan, followed by feeding to the column 40 ml aliquots of respective mixtures of ethyl acetate and chloroform (=2:8, 3:7, 4:6, 5:5, 6:4, 7:3, 8:2 and 9:1 by volume), chloroform, and methanol in this order. The eluate from the column was fractionated by 10 ml, and the 17th and 21st fractions were pooled and subjected to a thin layer chromatography using "SILICAGEL", a separatory thin layer commercialized by Merck & Co., Inc., NJ, USA, and a mixture solution of toluene, ethyl acetate, and acetic acid (=5:5:1 by volume) as a developer. After developing, a part of the silica gel at the position with an Rf of about 0.6 was scraped and extracted with an adequate amount of methanol to obtain a developed substance. The extract was evaporated to remove the solvent and dried into a 15.4 mg crystal of Compound 6.

Four grams of 4.6 g of the solid product, obtained from Fraction 4, were mixed with 40 ml methanol for dissolving, but partly were not dissolved to form a sediment. The sediment was collected, mixed with and sufficiently dissolved in 800 ml methanol, and allowed to stand at ambient temperature for two days to observe a red crude crystal. The crude crystal was collected, and the supernatant was allowed to stand under the same conditions as above to observe another red crude crystal. The newly formed crystal was collected and pooled with the previously obtained crystal, and the mixture was washed with an adequate amount of methanol, and dissolved in a sufficient amount of methanol. The resulting solution was filtered in a usual manner, and the filtrate was evaporated to remove the solvent and dried into a 44.5 mg crystal of Compound 7.

Although the concrete data are not shown, Fraction 5 was treated with columns of "FS-1830" and "SILICAGEL 60K650" similarly as applied for Fraction 3 and crystallized in methanol to obtain a crystal, namely Compound 8; and Fraction 6 was treated with a column of "FS-1830" similarly as applied for Fraction 3 and crystallized in acetonitrile to obtain a crystal, namely Compound 9.

Experiment 3
Identification of Compound 1

Experiment 3-1
Mass spectrum

Compound 1, obtained by the method in Experiment 2, gave a peak at m/z 249 ([M+H]$^+$) when measured for mass spectrum on fast atomic bombardment mass spectrometry (hereinafter abbreviated as "FAB-MS") and gave a peak at m/z 249.0694 ([M+H]$^+$) when measured on high resolution mass spectrometry.

Experiment 3-2
Magnetic resonance absorption spectrum

For Compound 1, obtained by the method in Experiment 2, it was measured for magnetic resonance absorption spectrum on $^1$H-nuclear magnetic resonance spectroscopic method and $^{13}$C-nuclear magnetic resonance spectroscopic method (hereinafter abbreviated as $^1$H-NMR and $^{13}$C-NMR, respectively).

The chemical shifts observed in each spectrum, and the assignments of hydrogen- and carbon-atoms are tabulated in Table 1.

TABLE 1

| Chemical shift δ (ppm) | Assignment |
| --- | --- |
| $^1$H-NMR | |
| 8.48 (1H, d, J = 7.9 Hz) | H-10 |
| 8.32 (1H, d, J = 7.7 Hz) | H-1 |
| 7.95 (2H, J = 3.7 Hz, 9.2 Hz) | H-3, H-4 |
| 7.88 (1H, d, J = 7.3 Hz) | H-7 |
| 7.87 (1H, t, J = 7.9 Hz) | H-9 |
| 7.74 (1H, m, J = 4.2 Hz) | H-2 |
| 7.48 (1H, t, J = 7.5 Hz) | H-8 |
| $^{13}$C-NMR | |
| 182.4 | C-6 |
| 157.6 | C-12 |
| 146.4 | C-5a |
| 145.9 | C-4a |
| 144.9 | C-10a |
| 137.7 | C-9 |
| 135.1 | C-3 |
| 129.8 | C-4 |
| 129.8 | C-2 |
| 126.9 | C-1 |
| 126.8 | C-8 |
| 124.7 | C-7 |
| 123.2 | C-12a |
| 122.2 | C-6a |
| 117.0 | C-10 |

Note: Measured in DMSO-d6.

Based on the experimental data, Compound 1 as the ethyl-soluble ingredient from the indigo plant was identified as 6,12-dihydro-6,12-dioxoindolo[2,1-b]quinazoline (tryptanthrin, $C_{15}H_8N_2O_2$, MW=248). The chemical structure of Compound 1 is as follows:

Chemical formula 1:

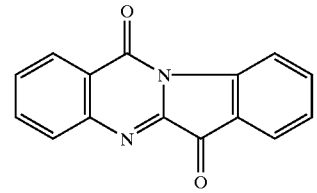

Experiment 4
Identification of Compound 2

Experiment 4-1
Melting point

For Compound 2 obtained by the method in Experiment 2, it was measured for melting point in a usual manner and revealed that it had a melting point of 298° C.

Experiment 4-2

Melting point
Ultraviolet absorption spectrum

For Compound 2 obtained by the method in Experiment 2, it was measured for ultraviolet absorption spectrum using methanol as a solvent in a usual manner and revealed that it had maximum absorption spectra at wavelengths of 206, 240, 273 and 353 nm.

Experiment 4-3

Infrared absorption spectrum

FIG. 1 is an infrared absorption spectrum of Compound 2 measured by the pressure tablet method using a powdery potassium bromide.

Experiment 4-4

Mass spectrum

For Compound 2 obtained by the method in Experiment 2, it was measured for mass spectrum on FAB-MS to find a peak at m/z 314 ($M^+$).

Experiment 4-5

Nuclear magnetic resonance absorption spectrum

For Compound 2 obtained by the method in Experiment 2, it was measured for nuclear magnetic resonance absorption spectrum on $^1$H-NMR and $^{13}$C-NMR. The chemical shifts and hydrogen- and carbon-atoms of the signals observed in each spectrum are tabulated in Table 2.

TABLE 2

| Chemical shift δ (ppm) | Assignment |
| --- | --- |
| $^1$H-NMR | |
| 8.06 (2H, d, J = 9 Hz) | H-2', H-6' |
| 6.94 (2H, d, J = 9 Hz) | H-3', H-5' |
| 6.90 (1H, s) | H-8 |
| $^1$H-NMR | |
| 6.15 (2H, s) | O—CH$_2$—O |
| $^{13}$C-NMR | |
| 176.2 | C-4 |
| 159.3 | C-4' |
| 153.7 | C-7 |
| 151.4 | C-9 |
| 147.4 | C-2 |
| 139.8 | C-5 |
| 135.8 | C-3 |
| 129.4 | C-2', C-6' |
| 128.7 | C-6 |
| 121.4 | C-1' |
| 115.4 | C-3', C-5' |
| 105.8 | C-10 |
| 102.6 | O—CH$_2$—O |
| 89.3 | C-8 |

Note: Measured in DMSO-d6.

Experiment 4-6

Elemental analysis

Conventional elemental analysis for Compound 2, obtained by the method in Experiment 2, resulted in C=59.2%, H=3.4%, O=37.4% and N<0.3% and revealed that Compound 2 has an experimental formula of $C_{16}H_{10}O7.3/5H_2O$.

Based on the data, Compound 2 as an ethyl acetate-soluble ingredient from the indigo plant was identified as 3,5, 4'-trihydroxy-6,7-methylenedioxy-flavone. The chemical formula of Compound 2 is in Chemical formula 2.

Chemical formula 2:

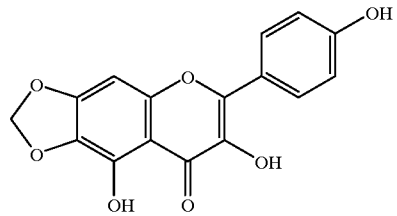

Experiment 5

Identification of Compound 3

Experiment 5-1

Thin layer chromatography

Compound 3 obtained by the method in Experiment 2, chlorogenic acid, quercetin, kaempferol, ferulic acid, cinnamic acid, coumaric acid, galangin, and pinocembrin, all of which were purchased from Sigma Chemical Company, St. Louis, Mo., USA, were subjected to conventional thin-layer chromatography. "KIESELGEL 60F$_{254}$" commercialized by Sigma Chemical Company, St. Louis, Mo., USA, was used as a thin layer plate, and a mixture solution of toluene, ethyl acetate, and acetic acid (=8:1:1 by volume) was used as a developing solvent system. After developing, the specimens on the plate were colored by the ultraviolet radiation at a wavelength of 254 nm. As a result, the Rf of Compound 3 was well coincided with that of kaempferol as a flavonoid.

Experiment 5-2

Melting point

For Compound 3 obtained by the method in Experiment 2, it was measured for melting point in a usual manner and revealed that it had a melting point of 277° C.

Experiment 5-3

Ultraviolet absorption spectrum

For Compound 3 obtained by the method in Experiment 2, it was measured for ultraviolet absorption spectrum using as a solvent methanol in a usual manner and revealed that it showed shoulder-like maximum absorption spectra at wavelengths of 265, 365 and 320 nm.

Experiment 5-4

Infrared absorption spectrum

Figure 2:
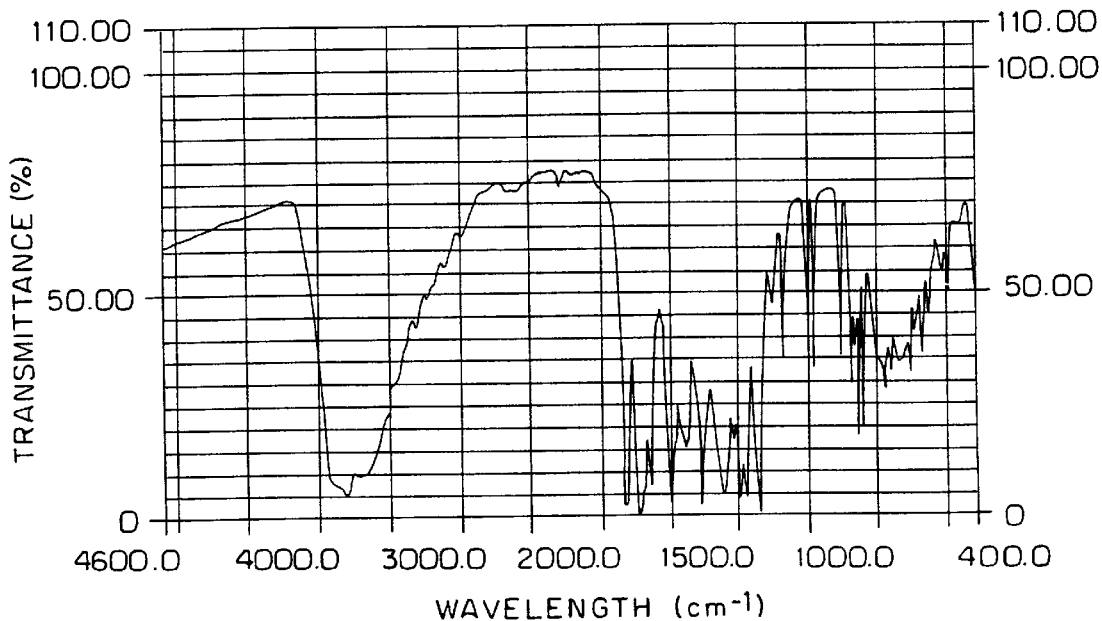
FIG. 2 is an infrared absorption spectrum of kaempferol, i.e., Compound 3.

FIG. 2 is an infrared absorption spectrum of Compound 3 measured by the pressure tablet method using a powdery potassium bromide.

Based on the data, Compound 3 as an ethyl acetate-soluble ingredient from the indigo plant was identified as kaempferol with a chemical formula of $C_{15}H_{10}O_6$ and a molecular weight of 286. The chemical formula of Compound 3 is in Chemical formula 3.

Chemical formula 3:

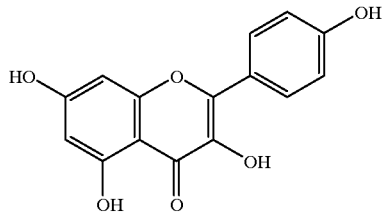

Experiment 6
Identification of Compound 4

Experiment 6-1
Melting point

Conventional analysis for melting point of Compound 4, obtained by the method in Experiment 2, revealed that the compound had a melting point of 272° C.

Experiment 6-2
Ultraviolet absorption spectrum

According to a usual manner, Compound 4 obtained by the method in Experiment 2 was measured for ultraviolet absorption spectrum using as a solvent methanol as solvent 1, methanol containing sodium methylate as solvent 2, methanol containing anhydrous aluminum chloride as solvent 3, or methanol containing anhydrous aluminum chloride and hydrochloric acid as solvent 4. The maximum absorption spectra under each solvent system are tabulated in Table 3.

TABLE 3

| Solvent | Maximum absorption (nm) |
|---|---|
| Solvent 1 | 255sh, 268, 335sh, 365 |
| Solvent 2 | 273, 320, 404 |
| Solvent 3 | 270, 305sh, 365sh, 425 |
| Solvent 4 | 270, 305sh, 365sh, 425 |

Note: The symbol "sh" represents that it showed a shoulder-like maximum absorption.

The results in Table 3 show that Compound 4 is a compound belonging to flavonol with hydroxy groups at C-3, C-7 and C-4' or at C-3, C-5, C-7 and C-4'.

Experiment 6-3
Nuclear magnetic resonance absorption spectrum

Compound 4, obtained by the method in Experiment 2, was measured for nuclear magnetic resonance absorption spectrum on $^1$H-NMR and $^{13}$C-NMR. The chemical shifts observed in each spectrum, and the assignments of hydrogen- and carbon-atoms are tabulated in Table 4.

TABLE 4

| Chemical shift δ (ppm) | Assignment |
|---|---|
| $^1$H-NMR | |
| 8.08 (2H, d, J = 8.97 Hz) | H-3', H-5' |
| 6.90 (2H, d, J = 8.97 Hz) | H-2', H-6' |
| 6.49 (1H, s) | H-8 |
| 3.88 (3H, s) | —O—CH$_3$ |
| $^{13}$C-NMR | |
| 177.7 | C-4 |

TABLE 4-continued

| Chemical shift δ (ppm) | Assignment |
|---|---|
| 160.7 | C-4' |
| 158.8 | C-7 |
| 153.8 | C-5 |
| 153.0 | C-9 |
| 148.4 | C-2 |
| 136.9 | C-3 |
| 132.4 | C-6 |
| 130.8 | C-2', C-6' |
| 123.8 | C-1' |
| 116.4 | C-3', C-5', |
| 105.0 | C-10 |
| 94.9 | C-8 |
| 61.0 | —O—CH$_3$ |

Note: Measured in deuterated methanol.

Experiment 6-4

Mass spectrum For Compound 4 obtained by the method in Experiment 2, it was measured in a usual manner for mass spectrum on electron ionization mass spectrometry (EI-MS) to show a peak at m/z 316 (M$^+$), and gave a peak at m/z 316.0486 (M$^+$) on high resolution mass spectrometry.

Experiment 6-5
Infrared absorption spectrum

Figure 3:
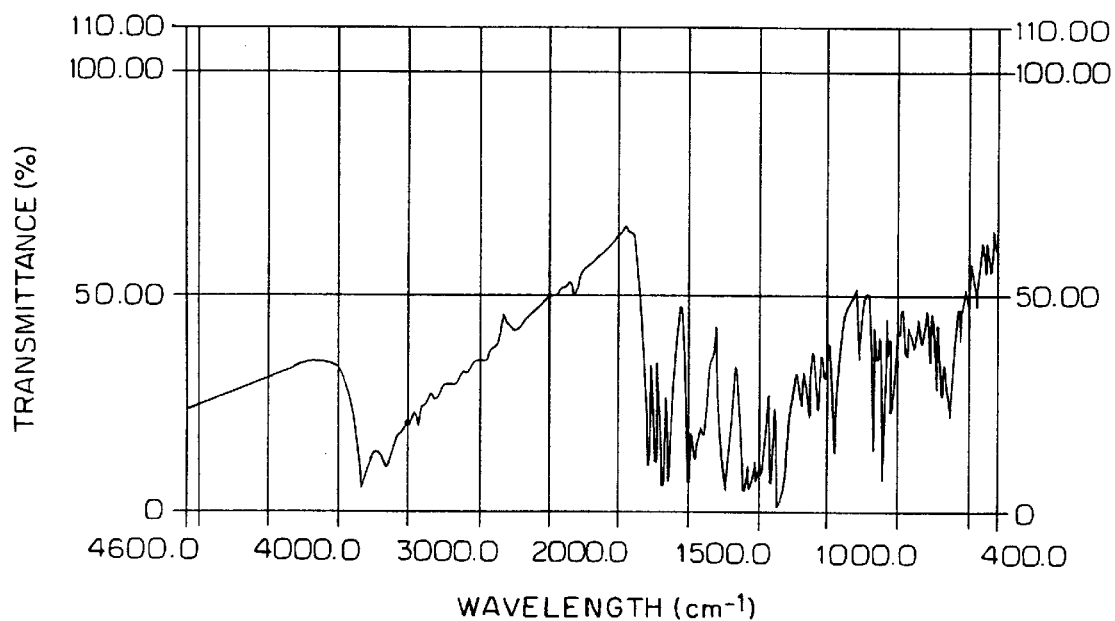
FIG. 3 is an infrared absorption spectrum of 3,5,7,4'-tetrahydroxy -6-methoxy-flavone, i.e., Compound 4.

FIG. 3 is an infrared absorption spectrum of Compound 4 measured on the pressure tablet method using a powdery potassium bromide.

Based on the data, Compound 4 as an ethyl acetate-soluble ingredient from indigo plant was identified as 3,5,7,4'-tetrahydroxy-6-methoxy-flavone with a chemical formula of $C_{16}H_{12}O_7$ and a molecular weight of 316. The chemical formula of Compound 4 is in Chemical formula 4.

Chemical formula 4:

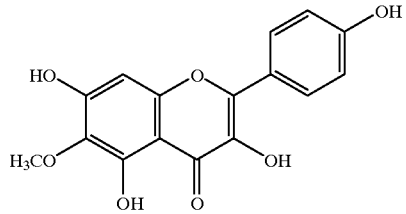

Experiment 7
Identification of Compound 5
Mass spectrum

For Compound 5 obtained by the method in Experiment 2, it was measured in a usual manner for mass spectrum on electron ionization mass spectrometry (EI-MS) to show a peak at m/z 170 (M$^+$).

Experiment 7-2
Nuclear magnetic resonance absorption spectrum

Compound 5, obtained by the method in Experiment 2, was measured for nuclear magnetic resonance absorption spectrum on $^1$H-NMR and $^{13}$C-NMR. The chemical shifts observed in each spectrum, and the assignments of hydrogen- and carbon-atoms are tabulated in Table 5.

TABLE 5

| Chemical shift δ (ppm) | Assignment |
| --- | --- |
| $^1$H-NMR | |
| 7.06 (2H, s) | H-2, H-6 |
| $^{13}$C-NMR | |
| 170.4 | C-7 |
| 146.5 | C-3, C-5 |
| 139.6 | C-4 |
| 122.1 | C-1 |
| 110.4 | C-2, C-6 |

Note: Measured in deuterated methanol.

Based on the data, Compound 5 as an ethyl acetate-soluble ingredient from indigo plant was identified as gallic acid with a chemical formula of $C_7H_6O_5$ and a molecular weight of 170. The chemical formula of Compound 5 is in Chemical formula 5.

Chemical formula 5:

Chemical formula 5:

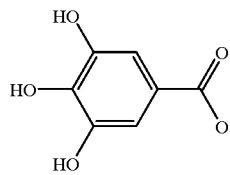

Experiment 8
Identification of Compound 6

Experiment 8-1
Mass spectrum

Compound 6, obtained by the method in Experiment 2, was measured in a usual manner for mass spectrum on electron ionization mass spectrometry (EI-MS) to show a peak at m/z 180 (M$^+$).

Experiment 8-2
Infrared absorption spectrum

Figure 4:
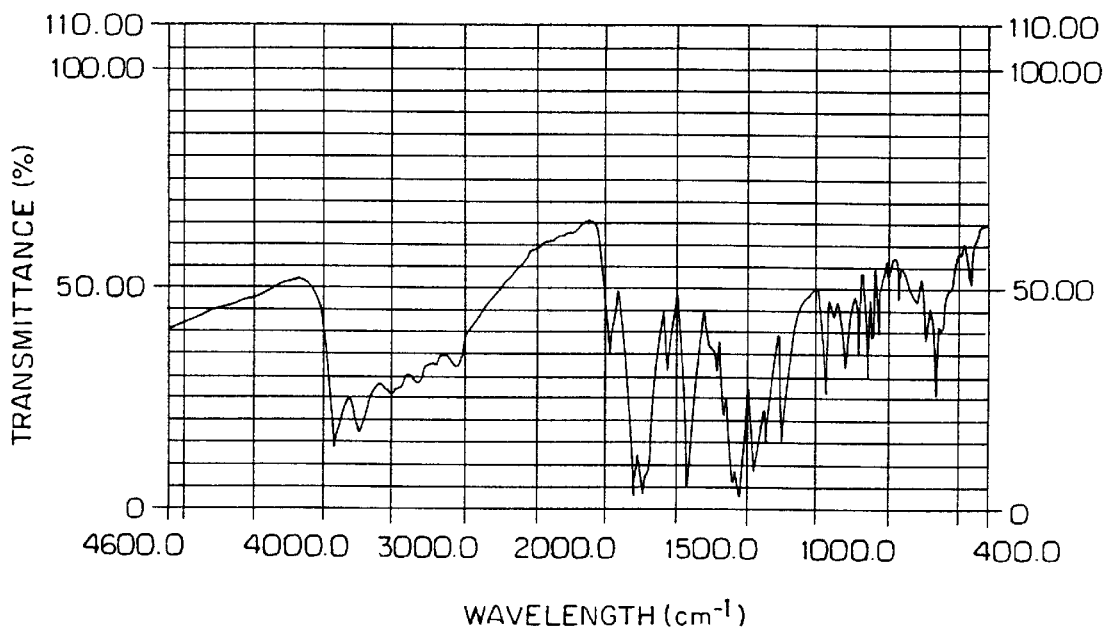
FIG. 4 is an infrared absorption spectrum of caffeic acid, i.e., Compound 6.

FIG. 4 is an infrared absorption spectrum of Compound 6 measured on the pressure tablet method using a powdery potassium bromide. Comparing with the infrared absorption spectrum of the known compound, the spectrum of the Compound 6 was well coincided with that of caffeic acid.

Experiment 8-3
Nuclear magnetic resonance absorption spectrum

For Compound 6, obtained by the method in Experiment 2, it was measured for nuclear magnetic resonance absorption spectrum on $^1$H-NMR and $^{13}$C-NMR. The chemical shifts observed in each spectrum, and the assignments of hydrogen- and carbon-atoms are tabulated in Table 6.

TABLE 6

| Chemical shift δ (ppm) | Assignment |
| --- | --- |
| $^1$H-NMR | |
| 7.43 (1H, d, J = 15.9 Hz) | H-7 |
| 7.03 (1H, d, J = 2.0 Hz) | H-2 |
| 6.91 (1H, dd, J = 2.0 Hz, 8.3 Hz) | H-6 |
| 6.77 (1H, d, J = 8.1 Hz) | H-5 |

TABLE 6-continued

| Chemical shift δ (ppm) | Assignment |
| --- | --- |
| 6.27 (1H, d, J = 15.6 Hz) | H-8 |
| $^{13}$C-NMR | |
| 148.9 | C-4 |
| 146.8 | C-3 |
| 144.7 | C-7 |
| 128.7 | C-1 |
| 122.4 | C-6 |
| 119.2 | C-8 |
| 116.5 | C-5 |
| 115.1 | C-2 |

Note: Measured in deuterated methanol.

Based on the data, Compound 6 as an ethyl acetate-soluble ingredient from the indigo plant was identified as caffeic acid with a chemical formula of $C_9H_8O_4$ and a molecular weight of 180. The chemical formula of Compound 6 is in Chemical formula 6.

Chemical formula 6:

Chemical formula 6:

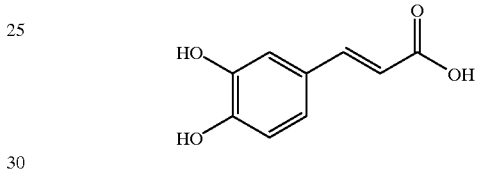

Experiment 9
Identification of Compound 7

Experiment 9-1
Mass spectrum

Compound 7 obtained by the method in Experiment 2, was measured in a usual manner for mass spectrum on electron ionization mass spectrometry (EI-MS) to show a peak at m/z 262 (M$^+$).

Experiment 9-2
Infrared absorption spectrum

Figure 5:
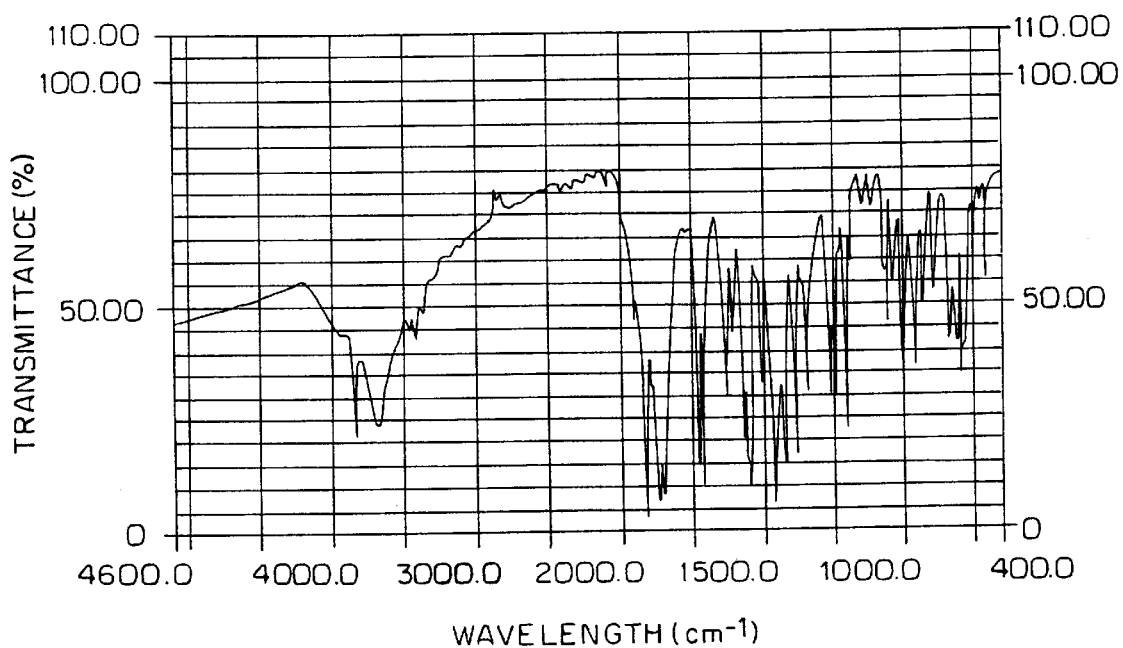
FIG. 5 is an infrared absorption spectrum of 3-(1,3-dihydro -3-oxo-2H-indol-2-ylidene)-1,3-dihydro-2H-indol-2-one, i.e., Compound 7.

FIG. 5 is an infrared absorption spectrum of Compound 7 measured on the pressure tablet method using a powdery potassium bromide. Comparing with the infrared absorption spectrum of the known compound, the spectrum of the Compound 7 was well coincided with that of 3-(1,3-dihydro-3-oxo-2H-indol-2-ylidene) -1,3-dihydro-2H-indol-2-one.

Experiment 9-3
Nuclear magnetic resonance absorption spectrum

For Compound 7, obtained by the method in Experiment 2, it was measured for nuclear magnetic resonance absorption spectrum on $^1$H-NMR and $^{13}$C-NMR. The chemical shifts observed in each spectrum, and the assignments of hydrogen- and carbon-atoms are tabulated in Table 7.

TABLE 7

| Chemical shift δ (ppm) | Assignment |
| --- | --- |
| $^1$H-NMR | |
| 11.00 (1H, s) | H-1 |
| 10.87 (1H, s) | H-1' |

TABLE 7-continued

| Chemical shift δ (ppm) | Assignment |
|---|---|
| 8.77 (1H, d, J = 7.81 Hz) | H-4' |
| 7.66 (1H, d, J = 7.57 Hz) | H-4 |
| 7.58 (1H, t, J = 8.06, 8.30 Hz) | H-6 |
| 7.42 (1H, d, J = 8.06 Hz) | H-7 |
| 7.26 (1H, t, J = 7.73 Hz, 7.57 Hz) | H-6' |
| 7.02 (2H, t, J = 7.57 HZ, 7.32 Hz) | H-5, H-5' |
| 6.91 (1H, d, J = 7.57 Hz) | H-7' |
| $^{13}$C-NMR | |
| 188.53 | C-3 |
| 170.86 | C-2' |
| 152.42 | |
| 140.83 | |
| 138.27 | |
| 137.01 | C-6' |
| 129.19 | C-6 |
| 124.59 | C-4' |
| 124.27 | C-4 |
| 121.39 | |
| 121.18 | C-5, C-5' |
| 118.97 | |
| 113.35 | C-7' |
| 109.49 | C-7 |
| 106.51 | |

Note: Measured in DMSO-d6.

Based on the data, Compound 7 as an ethyl acetate-soluble ingredient from the indigo plant was identified as 3-(1,3-dihydro-3-oxo-2H-indol-2-ylidene)-1,3-dihydro-2H-indol-2-one, i.e., indirubin with a chemical formula of $C_{16}H_{10}N_2O_2$ and a molecular weight of 262. The chemical formula of Compound 7 is in Chemical formula 7.

Chemical formula 7:

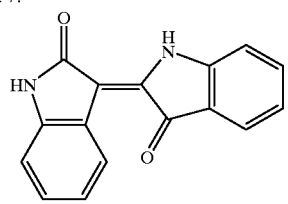

Similarly as the identification of Compounds 1 to 7, Compound 8 was identified, revealing that it was [3S-(3α, 4β, 21β)]9-ethyl-14-ethyl-21-(methoxycarbonyl)-4,8,13,18-tetramethyl -20-oxo-3-phorbinepropanoic acid), i.e., pheophorbide a with a chemical formula of $C_{35}H_{36}N_4O_5$ and a molecular weight of 592.69; and Compound 9 was identified, revealing that it was [3S-(3α, 4β, 21β)]9-ethyl-14-ethyl-21-(methoxycarbonyl )-4,8,13,18-tetramethyl -20-oxo-3-phorbinepropanoic acid methyl ester, i.e., methylpheophorbide a, $C_{36}H_{38}N_4O_5$, MW 606. The chemical formulae of Compound 8 as pheophorbide a, and Compound 9 as methyl-pheophorbide are respectively in Chemical formulae 8 and 9:

Chemical formula 8:

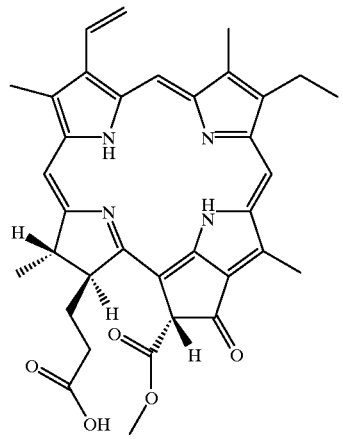

Chemical formula 9:

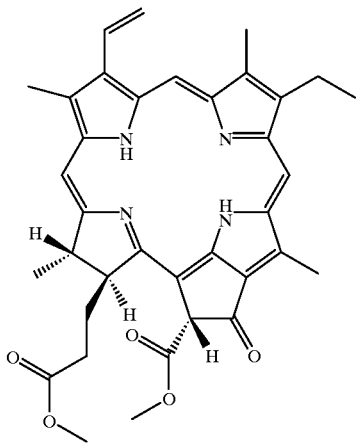

Experiment 10

Antiseptic action

For physiologically active extracts, obtained by the methods in Experiments 1 and 2, as shown in the following Table 8, they were examined for minimum inhibitory concentration (MIC) with respect to the bacteria in Table 6 by the agar plate dilution method using a streak smear. Brucella broth (BBL), containing 1.5 w/v % agar, 0.1 w/v % glucose, and 7 v/v % a germ-free horse defibrinated blood was used as a nutrient culture medium for Helicobacter pylori (NCTC 11638). For the other bacteria, a conventional medium for sensitivity disk was used. The results are in Table 8.

TABLE 8

| Pathogenic bacterium | Minimum inhibitory concentration (μg/ml) | | | | |
|---|---|---|---|---|---|
| | A | B | C | D | E |
| Helicobacter pylori (NCTC 11638) | 156 | 2.5 | 156 | 39.0 | 39.0 |
| Bacillus cereus (IFO 3466) | 156 | 39.0 | 313 | — | — |
| Pseudomonas aeruginosa (IFO 3453) | 78 | 39.0 | 313 | — | — |

TABLE 8-continued

| Pathogenic bacterium | Minimum inhibitory concentration (μg/ml) | | | | |
| --- | --- | --- | --- | --- | --- |
| | A | B | C | D | E |
| Staphylococcus aureus (ATCC 6538P) | 313 | 39.0 | 313 | — | — |

Note:
The symbol "—" represents that a test for minimum inhibitory concentration was not done.
The symbols "A", "B", "C", "D" and "E" represent the physiologically active extract of Experiment 1, Compound 1 of Experiment 2, Compound 2 of Experiment 2, Compound 3 of Experiment 2, and Compound 4 of Experiment 2, respectively.

The results in Table 8 show that the present physiologically active extract inhibited the growth of gram positive- and gram negative-bacteria. Among these extract and compounds, especially Compounds 1, 3 and 4 strongly inhibited the growth of *Helicobacter pylori* as a pathogenic bacterium for gastritis, gastric ulcer, duodenal ulcer, and gastric cancer.

Experiment 11
Antiviral action

According to a usual manner, FL cells (ATCC CCL62), an established cell line from a normal human amnion tissue, was subjected to monolayer culture on a microplate. The culture supernatant was removed from the microplate, and vesicular stomatitis virus (VSV) was adsorbed on the monolayer cells in a ratio of 0.1 plaque forming unit (PFU) per cell, followed by adding to the cells different concentrations of the physiologically active extracts in the following Table 9, obtained by the methods in Experiments 1 and 2 and dissolved in dimethylsulfoxide (DMSO), incubating the cells at 37° C. for 24 hours, disrupting the FL cells in the microplate by repeating the freezing and thawing, and centrifuging the microplate to obtain a culture supernatant containing VSV.

Thereafter, using L929 cells (RCB0081) derived from a mouse fibroblast, as a target cell, the test samples were examined for antiviral activity by conventional method using, as an index, cytopathic effect (CPE) by virus. The 50% growth inhibitory concentration of each physiologically active extract was calculated. The results are in Table 9.

TABLE 9

| Test sample | 50% Growth inhibitory concentration (μg/ml) |
| --- | --- |
| Physiologically active extract of Experiment 1 | 23 |
| Compound 1 of Experiment 2 | 13 |
| Compound 2 of Experiment 2 | 14 |

As shown in Table 9, it was confirmed that the present physiologically active extract exerted an antiviral action on a pathogenic virus. Under the conditions free of the virus, FL cells were cultured in a usual manner in the presence of or in the absence of each physiologically active extract under their 50% growth inhibitory concentrations determined in the above. As a result, no significant difference was found both in the growth and proliferation of the cells under each condition. Using the method with an index of the above CPE or a conventional method with an index of the plaque formation, the present physiologically active extract was examined for antiviral action to herpes simplex virus (HSV-1), influenza virus, vaccinia virus (VV), and mouse cytomegalovirus (MCMV). As a result, the present physiologically active extract was confirmed to have at least the same level of antiviral action on these pathogenic viruses as found in VSV. These data indicate that the present physiologically active extract exerts a strong antiviral action on pathogenic virus of animals and humans.

Experiment 12
Antitumor action

As shown in the following Table 10, either of the physiologically active extracts, obtained by the methods in Experiments 1 and 2, as test samples, was dissolved in DMSO to give a concentration of 10 mg/ml, diluted 50 times with RPMI1640 medium (pH 7.2) supplemented with 10 v/v % fetal calf serum, and distributed into a 96-well microplate in a volume of 100 μl/well. Solutions in each well were serially diluted with a fresh preparation of the same RPMI1640 medium (pH 7.2) as used in the above.

HL-60 cells (ATCC CCL-240) derived from a patient with acute promyelocytic leukemia, HGC-27 cells (RCB0500) derived from a patient with gastric cancer, and HLC-1 cells (RCB0083) derived from a patient with lung adenocarcinoma were respectively suspended in fresh preparations of the same RPMI1640 medium (pH 7.2) as used in the above to give respective cell concentrations of $4 \times 10^5$ cells/ml, $4 \times 10^5$ cells/ml, and $2 \times 10^6$ cells/ml. Each cell suspension was distributed to a microplate in a volume of 50 μl/well and incubated at 37° C. for 48 hours in a 5 v/v % $CO_2$ incubator. To each microplate, a 25 v/v % aqueous glutaraldehyde solution was added in a volume of 20 μl/well, and the microplate was allowed to stand for 15 min to fix the cells. Then, the cells adhered to the wells were washed with water, admixed with a 0.05 w/v % aqueous methylene blue solution in a volume of 100 μl/well, and further allowed to stand for 15 min to stain the cells. Thereafter, an excessive amount of the staining solution was removed from the wells by washing with water, and the cells were dried, admixed with 300 μl/well of 0.33 N hydrochloric acid, stirred sufficiently, and measured for absorption at a wavelength of 620 nm. In parallel, as a control, a system free of a test sample was provided and treated similarly as in the test samples. The 50% growth inhibitory concentration ($IC_{50}$) for each test sample was used as an index of antitumor action, and the samples were calculated for $IC_{50}$ by regarding the cell growth of control as 100%. The results are in Table 10.

TABLE 10

| Test sample | 50% growth inhibitory concentration (μg/ml) | | |
| --- | --- | --- | --- |
| | HL-60 cells | HGC-27 cells | HLC-1 cells |
| A | 24.9 | 61.5 | 276.8 |
| B | 4.2 | 1.5 | 2.2 |
| C | 243.7 | 37.1 | 40.4 |

Note:
The symbols "A", "B" and "C" represent that the physiologically active extract of Experiment 1, Compound 1 of Experiment 2, and Compound 2 of Experiment 2, respectively.

The results in Table 10 show that the present physiologically active extract effectively inhibits the growth of tumor cells of leukemia, gastric cancer, and lung cancer known as intractable malignant tumors. Particularly, Compound 1 showed a 10 times or higher antitumor action than Compound 2. These data show that the present physiologically active extract has a therapeutic/prophylactic effect on malignant tumors of mammals, including humans.

Experiment 13
Radical-entrapping action

As shown in Table 11, the radical-entrapping action of the physiologically active extracts, obtained by the methods in Experiments 1 and 2, was evaluated according to the nitro blue tetrazolium (NBT) method described by Toshio IMANARI in Igaku-no-Ayumi (Development of Medical Science), Vol. 101, pp. 496–497 (1977); The test samples were coexisted both in a coupled reaction system comprising a reaction where xanthin oxidase acts on xanthin to form superoxide and a reaction system where the formed superoxide converts NTB into formazan by the oxidization power. Then the formed formazan was quantified on spectrochemical analysis. Either of the present physiologically active extracts was dissolved in a refined water to give an appropriate concentration, and the solutions were used for test samples. As a control it was provided by replacing the test samples with a refined water. The 50% inhibitory activity for the formation of formazan in the control was defined as a one unit activity of radical-entrapping action. Based of the definition, the radical-entrapping activity of one gram of each test sample was determined. The results are in Table 11.

TABLE 11

| Test sample | Radical-entrapping action (unit/g) |
|---|---|
| Physiologically active extract of Experiment 1 | 27,800 |
| Compound 1 of Experiment 2 | — |
| Compound 2 of Experiment 2 | 1,830 |
| Compound 3 of Experiment 2 | 14,000 |
| Compound 4 of Experiment 2 | 4,010 |
| Compound 5 of Experiment 2 | 692,000 |
| Compound 6 of Experiment 2 | 418,000 |

Note:
The symbol "—" represents that the evaluation of the radical-entrapping action was impossible because the test sample did not sufficiently dissolve in water.

As shown in Table 11, the present physiologically active extract exerted a strong radical-entrapping action. Particularly, the radical-entrapping action of the physiologically active substance of Experiment 1 and Compounds 5 and 6 of Experiment 2 was remarkable. This indicates that the present physiologically active extract has properties of effectively entrapping in vivo radicals from active oxygen and lipoperoxide, and exerts a therapeutic/prophylactic effect on diseases relating to in vivo radicals such as malignant tumors, myocardial infarction, cerebral apoplexy, rheumatism, lifestyle related diseases or geriatric diseases, stresses, and aging. Compound 1 had an insufficient water-solubility; the evaluation of radical-entrapping action by the method in Experiment 13 was impossible.

Experiment 14
Apoptosis controlling action

Compound 1, obtained by the method in Experiment 2, was dissolved in DMSO to give a concentration of 0.8 mg/ml, and diluted with RPMI1640 medium (pH 7.2) supplemented with 10 v/v % fetal calf serum into a 20 $\mu$g/ml solution. The solution was distributed to a microplate in one milliliter per well, and the solution in each well was diluted in series with a fresh preparation of the same medium as used in the above.

HL-60 cells, ATCC CCL-240, derived from a patient with acute promyelocytic leukemia; U-937 cells, ATCC CRL-1593.2, derived from a patient with human histiocytic lymphoma; HGC-27 cells, RCB0500, derived from a patient with gastric cancer; HLC-1 cells, RCB0083, derived from a patient with lung adenocarcinoma; and $C_6$ cells, ATCC CCL-107, derived from rat glial tumor, were respectively suspended in RPMI1640 medium (pH 7.2) to give a cell density of $1 \times 10^6$ cells/ml or $2 \times 10^5$ cells/ml. To the microplate, containing a one milliliter dilution of 20, 10 or 5.0 $\mu$g/ml of Compound 1, was added one milliliter per well of either of the above cell suspensions and used for test systems. All the test systems were made duplex and respectively subjected to 24- and 48-hour incubations in a 5 v/v % $CO_2$ incubator at 37° C. A system free of Compound 1 was provided and treated similarly as above and used for control.

According to the method by I. Nicoletti et al. in *Journal of Immunological Methods*, Vol. 139, pp. 271–279 (1991), the apoptosis-induced cells in the test systems and control were stained by propidium iodide and determined for the percentage of the stained cells to the total cells in such a manner that transferring each of the cultures to polypropylene tubes, centrifuging the tubes, removing the resulting supernatants, washing the cells' sediments with phosphate buffered saline containing 0.3 v/v % calf serum albumin, and further centrifuging the washed cells to remove supernatants. The newly formed sediments were respectively mixed with 50 $\mu$g/ml of propidium iodide commercialized by Sigma Chemical Company, St. Louis, Mo., USA, 0.1 w/v % sodium citrate, and 0.1 w/v % "TRITON X-100", a surfactant commercialized by Sigma Chemical Company, St. Louis, Mo., USA, in respective volumes of 1.5 ml to stain the cells by propidium iodide. The stained cells were stored at 4° C. in the dark overnight. The stained cells of each test system were analyzed on "EPICS PROFILE II", a flow cytometry commercialized by Beckman Coulter, Inc., CA, USA. Based on the data the percentage of the stained cells to the total cells in each test system was measured for apoptosis occurrence. The results are in Table 12.

TABLE 12

| | | | Apoptosis occurrence (%) | | |
|---|---|---|---|---|---|
| | | | Compound 1 of Experiment 2 (concentration) | | |
| Cell line* | Culturing time (time) | Control | 2.5 $\mu$g/ml | 5.0 $\mu$g/ml | 10 $\mu$g/ml |
| HL-60 cells | 24 | 0.7 | 0.7 | 1.7 | 11.8 |
| ($5 \times 10^5$) | 48 | 1.5 | 1.3 | 4.2 | 22.6 |
| U-937 cells | 24 | 3.2 | 3.2 | 5.0 | 6.8 |
| ($5 \times 10^5$) | 48 | 4.5 | 5.2 | 11.7 | 66.9 |
| HGC-27 cells | 24 | 1.5 | 1.9 | 1.7 | 3.5 |
| ($1 \times 10^5$) | 48 | 1.4 | 2.2 | 4.1 | 14.1 |
| HLC-1 cells | 24 | 2.7 | 3.7 | 4.2 | 8.1 |
| ($1 \times 10^5$) | 48 | 1.5 | 5.8 | 7.3 | 21.8 |
| $C_6$ cells | 24 | 0.3 | 15.9 | 18.4 | 27.6 |
| ($1 \times 10^5$) | 48 | 0.4 | 38.4 | 64.8 | 67.1 |

Note:
The symbol "*" represents the initial cell density (cells/ml) in each culture.

As shown in Table 12, the apoptosis occurrence in each cell line increases depending on the dose of the present biologically active extract. Particularly, the difference between each of the test samples and controls showed a maximum level at a dose of 10 $\mu$g/ml of each extract. The present biologically active extract most remarkably promoted the apoptosis induction of U-937 cells derived from a lymphoma and $C_6$ cells derived from a glial tumor, among the cell lines. The tumorigenesis of cells is said to occur because apoptosis is not induced by some factors. In this experiment, the fact that a remarkable apoptosis is observed in the cells, cultured in the presence of the present physiologically active extract, indicates that the extract has an action of controlling apoptosis of living cells within normal conditions. Although the data are not shown, the same results similarly as in Compound 1 were obtained when the physiologically active extracts, excluding Compound 1, obtained by the methods in Experiments 1 and 2, were tested according to the above method.

Experiment 15

Action for controlling the production of cytokine

Compound 7 in Experiment 2 was dissolved in DMSO to give a concentration of one milligram per milliliter, diluted with RPMI1640 medium (pH 7.2) supplemented with 10 v/v % fetal calf serum (hereinafter designated as "serum medium" in Experiment 15) to give a concentration of 50 ng/ml, and further diluted in series with the serum medium.

HBL-38 cells as an immunocompetent cell were cultured until proliferated to a prescribed cell density. After culturing, the proliferated HBL-38 cells were washed three times with RPMI1640 medium (pH 7.2) (hereinafter designated as "serum-free medium" in Experiment 15) by centrifugation, and adjusted to give a cell density of $1 \times 10^8$ cells/ml using the serum-free medium. To one milliliter of the cell suspension were added 4.5 ml of the serum-free medium and 0.5 ml of a disperse solution prepared by dissolving dispase, commercialized by Godo Shusei, Co., Ltd., Tokyo, Japan, in physiological saline to give a concentration of 10,000 units/ml, and the mixture was incubated at 37° C. for 90 min under shaking conditions. Thereafter, HBL-38 cells were washed three times with the serum medium by centrifugation and mixed with the serum medium into a cell suspension with a cell density of $1 \times 10^6$ cells/ml.

Fifty micromilliliters of either of the above dilutes of Compound 7, 150 µl of the above cell suspension of HBL-38 cells treated with disperse, and 50 µl of a serum-free medium containing 5 µg/ml of lipopolysaccharide (LPS) were added to each well in a microplate, and the cells were incubated at 37° C. for 24 hours in a 5 v/v % $CO_2$ incubator and used for test group. In parallel, as a negative control, a system with a serum-free medium in place of the serum-free medium containing LPS in the test group, and, as a positive group, a system with a serum medium in place of the dilute of Compound 7 in the test group were provided and treated similarly as in test group. After 24-hour incubation, 50 µl aliquots of supernatants from each well were collected. The collected supernatants were respectively subjected to conventional enzyme immunoassay using Gg23-901-530, obtained from National Institute of Health, Bethesda, Md., USA, as a standard for human interferon-γ, and quantified for interferon-γ production in each system. The cells in each well, from which the supernatants were removed, were mixed with 50 µl aliquots of a $^3$H-thymidine solution with a radiation intensity of 5 µCi/ml in serum medium, and incubated at 37° C. for eight hours in a 5 v/v % $CO_2$ incubator. Thereafter, the cells in each well in the microplate were collected with a glass filter, measured for radiation intensity by "DIRECT β-COUNTER MATRIX 96", a β-ray detector commercialized by Packard Instrument Co., Conn., USA, and examined for $^3$H-thymidine uptake by the cells in each well. The results are in Table 13. In Table 13 the level of $^3$H-thymidine uptake is expressed with a relative value (%) to the positive control.

TABLE 13

| | Concentration of Compound 7 in Experiment 2 (ng/ml) | Interferon-γ production level (IU/ml) | Relative value of $^3$H-thymidine uptake (%) |
|---|---|---|---|
| Negative control | 0 | 1.367 | —** |
| Positive control | 0 | 5.468 | 100 |
| Test group | 0.07 | 2.753 | 98.0 |
| | 0.15 | 2.195 | 98.3 |
| | 0.31 | 1.979 | 99.7 |
| | 0.62 | 1.958 | 96.4 |
| | 1.25 | 1.288 | 99.6 |
| | 2.5 | 1.342 | 105.7 |
| | 5.0 | 0.932 | 101.1 |
| | 10.0 | 0.965 | 99.4 |

Note:
The symbol "*" represents a percentage to a measured value in positive control.
The symbol "**" represents that the $^3$H-thymidine uptake was not measured.

As shown in Table 13, LPS induced the interferon-γ production by HBL-38 cells, and Compound 7 as the present physiologically active extract inhibited the interferon-γ production dose-dependently. Under the concentration of at least 1.25 ng/ml of Compound 7, it inhibited the interferon-γ production to the same or lower level as that of the negative control free of LPS. While there found no significant difference between the control- and test-groups on the level of the $^3$H-thymidine uptake by HBL-38 cells. The results indicate that the present physiologically active extract does not affect the proliferation of immunocompetent cells and strongly inhibits the interferon-γ production by the cells induced by foreign substances for living bodies such as LPS. In place of the HBL-38 cells, mouse spleen cells as immunocompetent cells were prepared by conventional manner and treated similarly as above to examine the production of interleukin 10 in addition to the interferon-γ production. As a result, it was observed that the present physiologically active extract inhibits the interferon-γ production and augments the interleukin 10 production.

It is said that helper T-cells in the in vivo immune system are composed of a cell group comprising Th1 and Th2, and the balance between Th1 and Th2 greatly influences on the expression of immune functions. For example, diseases such as immune diseases including autoimmune- and inflammatory-diseases may be induced when the balance is out of the normal conditions for each living body to cause Th1-predominant conditions in the body. As examined in the above, interferon-γ and interleukin-10 are known that the former cytokine controls the balance to the Th1-predominant conditions, while the latter cytokine inhibits the balance not to tend to the Th1-predominant conditions. These experimental data indicate that the present physiologically active extract has an action of controlling the production of cytokines by immunocompetent cells to control the balance in vivo to the normal conditions, and effectively treats/prevents the diseases induced by the abnormality of the balance. Since interferon-γ is known as an inflammatory cytokine, the above data also indicate that the present physiologically active extract can be also useful as an inhibitor for the production of such cytokines. As the data is not shown, the resting present physiologically active extracts in Experiments 1 and 2 were confirmed that they exerted a similar action as Compound 7, though the activities were varied.

The results in Experiments 1 to 15 indicate that the present physiologically active extracts as the ethyl acetate-soluble ingredients obtained by the method in Experiment 1, i.e., 6,12-dihydro-6,12-dioxoindolo[2,1-b]quinazoline; 3,5, 4'-trihydroxy -6,7-methylenedioxy-flavone; kaempferol; 3,5,7,4'-tetrahydroxy -6-methoxy-flavone; gallic acid; caffeic acid; 3-(1,3-dihydro-3-oxo-2H-indol-2-ylidene)-1,3-dihydro-2H-indol-2-one; [3S-(3α, 4β, 21β)]9-ethyl-14-ethyl-21-(methoxycarbonyl) -4,8,13,18-tetramethyl-20-oxo-3-phorbinepropanoic acid); and [3S-(3α, 4β, 21β)]9-ethyl-14-ethyl-21-(methoxycarbonyl)-4,8,13,18-tetramethyl -20-oxo-3-phorbinepropanoic acid methyl ester exert a variety of physiological actions including antiviral-, antitumor-, radical entrapping-, and apoptosis controlling-actions, as well as cytokine production controlling- or inhibiting-actions.

Experiment 16
Acute toxicity test

According to a usual manner, the oral-, intravenous-, and intraperitoneal-administrations of the physiologically active extracts, obtained by the methods in Experiments 1 and 2, to ddy mice, five weeks old, resulted in an $LD_{50}$ of over one g/kg body weight independent of their administration routes. The data show the present physiologically active extracts are safely administered to mammals including humans with lesser side effects.

The preferred embodiments according to the present invention are described with reference to the following Examples:

Example 1
Crude physiologically active extract

Thirty kilograms of an aerial part of an indigo plant, grown in Aki-city, Shimane-prefecture, Japan, were harvested in July, pulverized, and extracted three times repeatedly at ambient temperature with 30–60 l ethyl acetate for each extraction. The resulting extracts were pooled and filtered with a filter paper, and the filtrate was collected, subjected to evaporation for removing ethyl acetate, and dried into a 168 g extract containing ethyl acetate-soluble ingredients from the indigo plant.

The extract with a variety of physiological actions is useful as a crude drug used in cosmetics and pharmaceuticals.

Example 2
Purified physiologically active extract

An extract obtained by the method in Example 1 was suspended in 50 v/v % aqueous methanol solution and divided into eight aliquots which were then separatory fed to a column packed with 1,700 ml of "FS-1830", a gel for adsorption chromatography commercialized by Japan Organo Co., Ltd., Tokyo, Japan, and fed successively with 60, 70, 80, and 90 v/v % aqueous methanol solutions, methanol, and ethyl acetate in an equal amount to the gel volume. The eluate was fractionated in every half volume of the gel volume. The former and latter fractions, Fraction 2 and Fraction 1 respectively, eluted from the column with 80 v/v % aqueous methanol solution; the latter fraction, Fraction 3, eluted from the column with 60 v/v % aqueous methanol solution; and the latter fraction, Fraction 4, eluted from the column with 90 v/v % aqueous methanol solution, were separately collected, evaporated to remove solvent, and dried into solid products.

From among 5.2 g of the solid product from Fraction 1, 2.6 g of which was suspended in 30 ml methanol and filtered by suction to separate into a soluble part and an insoluble part (876 mg). The solution of the soluble part was fed to a column packed with 1,350 ml of silica gel and fed with a linear gradient of a mixture solution of chloroform and methanol increasing step-wisely from 5 v/v % to 100 v/v % methanol, followed by collecting the eluate 450 ml a fraction. Fraction 4 was evaporated to remove solvent, and the resulting solid product was suspended in two milliliters of methanol, and washed by filtering under suction conditions to obtain a 19.4 mg crystal of 6,12-dihydro -6,12-dioxoindolo[2,1-b]quinazoline. The insoluble fraction was dissolved in an adequate amount of methanol and allowed to stand at ambient temperature to obtain a 278 mg yellow needle-like crystal of 3,5,4'-trihydroxy-6,7-methylenedioxy-flavone.

10.7 g of the solid product from Fraction 2 was dissolved in 40 ml methanol, and the solution was fed to a column packed with 1,520 ml of "SEPHADEX LH-20", a gel for adsorption chromatography commercialized by Pharmacia LKB Biotechnology AB, Uppsala, Sweden, followed by collecting the eluate 190 ml a fraction. The 15th and 18th fractions were respectively evaporated to remove the solvents and dried into solid products. Four hundred milligrams of the solid composition obtained from the 18th fraction was admixed with and completely dissolved in an about 210 ml mixture solution of methanol and water (=5:2 by volume). The solution was filtered with a 0.22 μm membrane filter and allowed to stand at ambient temperature for three days to find the formation of a crystal. Using a conventional filter paper, the crystal was collected to obtain a 89.3 mg crystal of kaempferol. Five hundred milligrams of the solid product from the 15th fraction was suspended in 10 ml methanol and filtered to collect insoluble substances. Then the insoluble substances were admixed with and completely dissolved in 250 ml methanol. The solution was filtered with a 0.22 μm membrane filter and allowed to stand at ambient temperature for seven days to find a crystal. With a conventional filter paper, the crystal was collected to obtain a 252.3 mg crystal of 3,5,7,4'-tetrahydroxy -6-methoxy-flavone.

11.8 g of the solid product from Fraction 3 was dissolved in 40 ml methanol, and the solution was fed to a column packed with 1,680 ml of "SEPHADEX LH-20", a gel for adsorption chromatography commercialized by Pharmacia LKB Biotechnology AB, Uppsala, Sweden, followed by collecting the eluate 560 ml a fraction. The 4th fraction was respectively evaporated to remove the solvent and dried into a solid product. Then the solid product was dissolved in an about 10 ml methanol, and the solution was fed to a column packed with 480 ml of "FS-1830", a gel for adsorption chromatography commercialized by Japan Organo Co., Ltd., Tokyo, Japan, fed successively with 0, 10, 20, 30, 40, 50, 60 and 70 v/v % aqueous methanol solutions in respective volumes of 480 ml, and further fed with 960 ml methanol. The eluate was fractionated 240 ml a fraction, and the 5th fraction was evaporated to remove the solvent and dried into a 150 mg solid product. Then the solid product was dissolved in 300 ml ethyl acetate, and the solution was filtered with a 0.22 μm membrane filter and allowed to stand at ambient temperature for seven days to find the formation of a crystal. Using a conventional filter paper, the crystal was collected to obtain a 18.7 mg crystal of gallic acid. The 9th fraction, eluted from the column of "FS-1830", was evaporated to remove the solvent and dried into a 500 mg solid product. The solid product was dissolved in 0.5 ml ethyl acetate, and the solution was fed to a column packed with 40 ml of "SILICAGEL 60K650", a gel for adsorption chromatography commercialized by Katayama Chemical Industries Co., Ltd., Tokyo, Japan, and fed successively with 40 ml aliquots of the mixture solutions of ethyl acetate and chloroform (=2:8, 3:7, 4:6, 5:5, 6:4, 7:3, 8:2 and 9:1 by volume), chloroform, and ethanol. The eluate from the column was fractionated 10 ml a fraction, and the 17th and 21st fractions were pooled and subjected to thin layer chromatography using "SILICAGEL 60F$_{254}$ (product No. 5717)", a separatory thin layer commercialized by Merck & Co., Inc., NJ, USA, was used as a thin layer plate, and a mixture solution of toluene, ethyl acetate, and acetic acid (=5:5:1 by volume) as a developing system. After developing, a part of the silica gel at the position with an Rf value of about 0.6 was scraped and extracted with an adequate amount of methanol to obtain a developed substance. The solvent was removed from the extract by an evaporator and dried into a 15.4 mg crystal of caffeic acid.

Four grams of the 4.6 g solid product from Fraction 4 was admixed with and allowed to dissolve in 40 ml methanol, but the solid product partly sedimented without dissolving. The sediment was collected, dissolved sufficiently in 800 ml methanol, and allowed to stand at ambient temperature for two days to find a crystallized red crude crystal. The crude crystal was collected, and the remaining supernatant was allowed to stand similarly as above to find again a crystallized red crude crystal. The crude crystal thus obtained was collected and pooled with the previously obtained red crude crystal, and the mixture was washed with an adequate amount of methanol and dissolved in a sufficient amount of methanol. The resulting solution was membrane filtered, and the filtrate was evaporated to remove the solvent and dried into a 44.5 mg crystal of 3-(1,3-dihydro -3-oxo-2H-indol-2-ylidene)-1,3-dihydro-2H-indol-2-one.

These compounds with a variety of physiological actions are useful as crude drugs for cosmetics and pharmaceuticals which require a relatively-highly purified ingredient.

Example 3
Crude physiologically active extract

Fifteen kilograms of an aerial part of an indigo plant, grown in Aki-city, Shimane-prefecture, Japan, were harvested in July, pulverized, and extracted three times repeatedly at ambient temperature with 30 l ethanol for each extraction. The resulting extracts were pooled and filtered with a filter paper, and the filtrate was collected, subjected to evaporation for removing ethanol, and dried into a 560 g extract containing ethyl acetate-soluble ingredients from the indigo plant. Using as a standard specimen the compound obtained by the method in Example 2, the above physiologically active extract was analyzed on conventional high-performance liquid chromatography or gas chromatography and revealed that the extract contained, as ethyl acetate-soluble ingredients, 6,12-dihydro-6,12-dioxoindolo[2,1-b] quinazoline; 3,5,4'-trihydroxy-6,7-methylenedioxy-flavone; kaempferol; 3,5,7,4'-tetrahydroxy-6-methoxy-flavone; gallic acid, caffeic acid, 3-(1,3-dihydro-3-oxo-2H-indol-2-ylidene)-1,3-dihydro-2H-indol -2-one, [3S-(3α, 4β, 21β)]9-ethyl-14-ethyl-21-(methoxycarbonyl) -4,8,13,18-tetramethyl-20-oxo-3-phorbinepropanoic acid), and [3S-(3α, 4β, 21β)]9-ethyl-14-ethyl-21-(methoxycarbonyl) -4,8, 13,18-tetramethyl-20-oxo-3-phorbinepropanoic acid methyl ester in respective amounts of 65, 780, 354, 988, 250, 230, 75, 52 and 63 mg.

The product with a variety of physiological actions is useful as a crude drug used in foods, cosmetics, and pharmaceuticals.

Example 4
Refreshment

According to a usual manner, potatoes, which reducing sugars had been self-assimilated by storing at 20° C. and a relative humidity of 85% for two weeks, were washed with water, pealed, graded, and sliced with a centrifugal slicer into slices, about 1.5 mm thick. The slices were washed with water to remove starches on their surfaces, drained of water, fried in oil at 170° C. for about five minutes, and drained of excessive oil. Using a salter, the fried slices were homogeneously sprayed with a powdery seasoning containing six parts by weight of salt, three parts by weight of "TREHAOSE®", a food grade trehalose powder with a trehalose purity of at least 98% commercialized by Hayashibara Shoji, Inc., Okayama, Japan, one part by weight of a physiologically active extract obtained by the method in Example 3, and an adequate amount of a spice. The resulting slices were transferred to a machine for weighing, injected, and packed into a refreshment.

The product with a satisfactory flavor and taste can be arbitrarily used as a health food for maintaining/promoting the health.

Example 5
Tea bag

Nine parts by weight of a freeze-dried tea extract were dissolved in an adequate amount of water, and the solution was mixed with one part by weight of a physiologically active extract, which had been obtained by the method in Example 3 and dissolved in ethanol. The mixture was sprayed over 90 parts by weight of tea leaves which had been in a usual manner fermented and dried. Then, the leaves were sieved, cut, dried for finish, allowed to remove impurities by a separator, and packed with a Japanese paper two grams a portion into a tea bag.

For drinking, the product is soaked in a 180 ml cold water for about 10 min or in a 180 ml hot water heated to 90–100° C. for about two minutes. The product with a satisfactory flavor and taste can be arbitrarily used as a health food for maintaining/promoting the health.

Example 6
Supplemental health food

Fifty-two parts by weight of "TREHAOSE®", a food grade trehalose powder with a trehalose purity of at least 98% commercialized by Hayashibara Shoji, Inc., Okayama, Japan, 40 parts by weight of corn starch, 3.5 parts by weight of a physiologically active extract obtained by the method in Example 3, and 2.5 parts by weight of a cellulose crystal were mixed. The mixture was in a usual manner kneaded with water by dropping water thereunto, subjected to fluidized-granulation method, pulverized, and sized to obtain a powder for tabletting. The powder was mixed to homogeneity with two parts by weight of sucrose fatty acid ester, and the mixture was tabletted by a tabletting machine with a punch, 11 mm in diameter, into tablets, about 300 mg each.

The product is easily swallowable and satisfactorily disintegrated in the tracts and can be arbitrarily used as a health food for maintaining/promoting the health.

Example 7
Hair rinse

One part by weight of "TREHAOSE®", a food grade trehalose powder with a trehalose purity of at least 98% commercialized by Hayashibara Shoji, Inc., Okayama, Japan, two parts by weight of a physiologically active extract obtained by the method in Example 1, two parts by weight of "αG RUTIN", an α-glucosyl rutin commercialized by Toyo Sugar Refining Co., Ltd., Tokyo, Japan, two parts by weight of distearyl methyl ammonium chloride, two parts by weight of cetanol, two parts by weight of silicon oil, one part by weight of polyoxyethylene oleyl alcohol ether, and an adequate amount of a flavor were dissolved by heating. The solution was mixed under stirring conditions with a mixture of three parts by weight of 1,3-butyleneglycol, 85 parts by weight of refined water, and an adequate amount of an antiseptic, followed by cooling the mixture into a hair rinse.

The product, having a satisfactory stability and a lesser stimulation to the scalp, can be arbitrarily used as a cosmetic for maintaining/promoting the healthy conditions of the scalp and hair.

Example 8

Milky lotion

According to conventional manner, 0.5 part by weight of polyoxyethylene behenyl ether, one part by weight of polyoxyethylene sorbitol tetraoleate, one part by weight of oil-soluble glycerol monostearate, 0.5 part by weight of pyruvic acid, 0.3 part by weight of behenyl alcohol, 0.3 part by weight of maltitol, one part by weight of avocado oil, one part by weight of a physiologically active extract obtained by the method in Example 1, and adequate amounts of vitamin E and an antiseptic were dissolved by heating. The solution was mixed with one part by weight of sodium L-lactate, seven parts by weight of 1,3-butyleneglycol, 0.1 part by weight of carboxyvinyl polymer and 86.3 parts by weight of refined water, and the mixture was emulsified with a homogenizer into a milky lotion.

The product is less sticky and satisfactorily extendable and can be arbitrarily used as a cosmetic for maintaining/promoting the healthy conditions of the skin.

Example 9

Toothpaste

A toothpaste was obtained by mixing 45 parts by weight of calcium secondary phosphate, 2.9 parts by weight of pullulan, 1.5 parts by weight of sodium lauryl sulfate, 20 parts by weight of glycerine, 0.5 part by weight of polyoxyethylene sorbitan laurate, 10 parts by weight of sorbitol, seven parts by weight of maltitol, 13 parts by weight of refined water, and 0.1 part by weight of a physiologically active extract obtained by the method in Example 1.

The product can be arbitrarily used as a cosmetic for maintaining/promoting the healthy conditions in the oral cavity.

Example 10

Ointment

According to conventional manner, one part by weight of sodium acetate, trihydrate, four parts by weight of DL-calcium lactate, 10 parts by weight of glycerine, 0.5 part by weight of peppermint oil, 49 parts by weight of petrolatum, 10 parts by weight of Japan wax, 10 parts by weight of lanolin, 14.5 parts by weight of sesame oil, and two parts by weight of a composition incorporated, based on the percentage of the extract in Example 1, with the seven types of Compounds 1 to 7 as physiologically active extracts obtained by the method in Example 2, were mixed to homogeneity into an ointment.

The product, having a satisfactory permeability and extensibility, can be arbitrarily used as a medicament for maintaining/promoting the health conditions of the skin.

[Effect of the Invention]

As described above, the present invention was made based on the self-finding that ethyl acetate-soluble ingredients from a raw indigo plant exert a variety of physiological actions on mammals and humans. When administered to mammals and humans, the above ingredients exert physiological actions including antiseptic-, antiviral-, antitumor-, radical entrapping-, apoptosis controlling-, cytokine production controlling-, cytokine production inhibiting-, and nitrogen monoxide synthetic enzyme expression inhibitory-actions. Thus, the present physiological active extract containing the ethyl acetate-soluble ingredients can be widely used in the food-, cosmetic- and pharmaceutical-fields.

Conventional leaves and seeds of indigo plants, prepared by drying under the sun, are used after extracted with hot water; substantially used are the water-soluble ingredients of the indigo plants. Among these ingredients, indole compounds are susceptible to chemical changes such as hydrolysis and air-oxidization during the drying under the sun, and may possibly be deteriorated. The physiologically active composition according to the present invention can be prepared by using the ethyl acetate-soluble ingredients from raw indigo plants without drying the plant under the sun; the present invention enables the use of the intact physiologically effective ingredients in a living indigo plant at any time and any place, i.e., even if the places were far from the indigo plant-producing district. The present physiologically active extract with such usefulness can be produced in a desired amount by the present process using a raw indigo plant as a material.

The present invention with these useful effects is a significant invention that will strongly contribute to this field.

While there has been described what is at present considered to be the preferred embodiments of the invention, it will be understood the various modifications may be made therein, and it is intended to cover the appended claims all such modifications as fall within the true spirits and scope of the invention.

We claim:

1. A physiologically active extract, comprising as active ingredients two or more ethyl acetate-soluble ingredients, said extract being prepared by a process comprising a step of extracting a raw indigo plant with ethyl acetate and evaporating the ethyl acetate therefrom, said ingredients being selected from the group consisting of 6,12-dihydro-6,12-dioxoindolo [2,1-b]quinazoline, 3,5,4'-trihydroxy-6,7-methylenedioxy-flavone; kaempferol, 3,5,7,4'-tetrahydroxy-6-methoxy-flavone, gallic acid, caffeic acid, 3-(1,3-dihydro-3-oxo-2H-indol-2-ylidene) -1,3-dihydro-2H-indol-2-one, [3S-(3α, 4β, 21β)]9-ethyl-14-ethyl -21- (methoxycarbonyl)-4,8,13,18-tetramethyl-20-oxo-3-phorbinepropanoic acid, and [3S- (3α, 4β, 21β)]9-ethyl-14-ethyl -21- (methoxycarbonyl)-4,8,13,18-tetramethyl-20-oxo-3-phorbinepropanoic acid methyl ester, wherein said extract is in an amount effective for exerting the following properties and physiological actions on mammals:

a. inhibiting the growth of gram-positive and gram-negative microorganisms;

b. inhibiting the growth of pathogenic viruses;

c. inhibiting the growth of tumor cells of incurable tumors;

d. entrapping radicals derived from active oxygen and lipoperoxide that induce malignant tumors, myocardial infarction, cerebral apoplexy, rheumatism, and lifestyle related diseases;

e. acting on normal and abnormal B-cells, T-cells, nerve cells, epithelial cells of the digestive tract, stem cells of the digestive tract, vascular endothelial cells, and skin cells to regulate the apoptosis of said cells within normal condition to treat diseases of digestive organs, circulatory organs, eyes, ears, nose, throat, skin, nerves, and bones;

f. controlling the production of cytokines by immuno-competent cells which controls the balance in vivo of type 1 helper T-cells and type 22 helper T-cells to treat diseases selected from the group consisting of autoimmune diseases, hepatic disorders, renal disorders, pancreatic disorders, and graft-vs.-host diseases; and g. inhibiting the expression of nitrogen monoxide synthesizing enzymes by cells in vivo, which expression is induced by cytokines and endotoxins, and inhibiting the formation of nitrogen monoxide to treat diseases selected from the group consisting of autoimmune disease, allergic disease, inflammatory disease, malignant tumors, renal disorders, and lung disorders.

2. The extractof claim 1, which contains said ethyl acetate-soluble ingredients in an amount of at least 0.01%, on a dry solid basis.

3. The extract of claim 1 wherein one of said two or more ingredients is 6,12-dihydro-6,12-dioxoindolo [2,1-b] quinazoline.

4. The extract according to claim 1 wherein the microorganisms are selected from the group consisting of *Helicobacter pylon;* wherein the pathogenic viruses are selected from the group consisting of influenza virus, vesicular stomatitis virus, herpes simplex virus, vaccinia virus, and cytomegalovirus;

wherein the tumor cells of incurable tumors are selected from the group consisting of leukemia, gastric cancer, and lung cancer cells; and wherein the cytokines are selected from the group consisting of interferon-gamma and interleukin 10.

5. A physiologically active composition, comprising the extract of claim 1.

6. The composition of claim 5, which further contains one or more members selected from the group consisting of water, alcohols, amylaceous substances, proteins, fibers, saccharides, lipids, fatty acids, vitamins, minerals, flavors, colors, sweeteners, seasonings, spices and antiseptics.

7. The composition of claim 5, which is used as a food product, cosmetic, or pharmaceutical.

8. The composition of claim 7, which is a pharmaceutical, wherein said pharmaceutical is a member selected from the group consisting of an antiseptic, antiviral agent, antitumor agent, radical-entrapping agent, apoptosis-controlling agent, agent for controlling or inhibiting the production of cytokines, agent for inhibiting the expression of nitrogen monoxide synthetic enzymes, agent for neovascular inhibition, and agent for improving the sleep disturbance.

9. The composition of claim 5, which contains said ethyl acetate-soluble ingredients in an amount of at least 0.005%, on a dry solid basis.

10. The composition of claim 5 comprising all of said ethyl acetate-soluble ingredients.

11. A process for producing the extract of claim 1, comprising the steps of soaking a raw indigo plant in ethyl acetate to extract ethyl acetate-soluble ingredients of said indigo plant, and collecting the extract.

12. The process of claim 11, wherein said indigo plant is either a portion of or the whole of a fresh aerial part of said indigo plant.

13. An extract obtained by the process of claim 12.

14. In a method for the manufacture of a food product comprising mixing edible components, the improvement wherein one said edible component is the extract of claim 1.

15. In a method of making a cosmetic comprising mixing cosmetic-forming components, the improvement wherein one said cosmetic forming component is the extract of claim 1.

16. In a method of forming a pharmaceutical composition comprising mixing at least one active agent with a pharmaceutical excipient, the improvement wherein said active agent comprises the extract of claim 1.

17. In a method for the treatment of a viral disease comprising administering an antiviral agent to a patient in need thereof, the improvement wherein said antiviral agent is the extract of claim 1.

18. In a method for the treatment of a tumor comprising administering to a patient in need thereof an anti-tumor agent, the improvement wherein said antitumor agent is the extract of claim 1.

19. In a method for radical-entrapment, apoptosis control, inhibition or control of the production of cytokines, inhibition of expression of nitrogen monoxide synthetic enzymes, or neovascular inhibition in a patient in need of one of said therapies, comprising administering to said patient a radical-entrapping agent, an apoptosis-controlling agent, an agent for controlling or inhibiting the production of cytokines, an agent for inhibiting the expression of nitrogen monoxide synthetic enzymes, or an agent for neovascular inhibition, the improvement wherein said agent comprises the extract of claim 1.

20. In a method for the treatment of sleep disturbance comprising administering to a patient in need thereof an agent for improving sleep, the improvement wherein said agent is the extract of claim 1.

* * * * *